(12) United States Patent
Bartels et al.

(10) Patent No.: US 10,941,147 B2
(45) Date of Patent: Mar. 9, 2021

(54) BICYCLIC HETEROARYL DERIVATIVES

(71) Applicant: Hoffmann-La Roche Inc., Little Falls, NJ (US)

(72) Inventors: Bjoern Bartels, Schopfheim (DE); Roland Jakob-Roetne, Inzlingen (DE); Anja Limberg, Frankfurt (DE); Werner Neidhart, Basel (CH); Hasane Ratni, Habsheim (FR); Michael Reutlinger, Freiburg (DE); Jérôme Charles Sarie, Basel (CH); Greta Vastakaite, Zurich (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/346,623

(22) PCT Filed: Oct. 30, 2017

(86) PCT No.: PCT/EP2017/077719
§ 371 (c)(1),
(2) Date: May 1, 2019

(87) PCT Pub. No.: WO2018/083050
PCT Pub. Date: May 11, 2018

(65) Prior Publication Data
US 2019/0284191 A1 Sep. 19, 2019

(30) Foreign Application Priority Data
Nov. 1, 2016 (EP) ..................... 16196720

(51) Int. Cl.
C07D 487/04 (2006.01)
(52) U.S. Cl.
CPC .................. C07D 487/04 (2013.01)
(58) Field of Classification Search
CPC .................................................. C07D 487/04
(Continued)

(56) References Cited

U.S. PATENT DOCUMENTS

| 8,349,880 | B2 | 8/2013 | Marcin et al. |
| 8,703,763 | B2 | 4/2014 | Baumann et al. |
| 10,562,903 | B2 * | 2/2020 | Bartels ................. C07D 471/04 |

FOREIGN PATENT DOCUMENTS

WO    2012/116965 A1    9/2012

OTHER PUBLICATIONS

Bai, X., et al., "An atomic structure of human γ-secretase" NATURE 525:212-217 (Sep. 10, 2015).

Beher et al., "Selected Non-steroidal Anti-inflammatory Drugs and Their Derivatives Target g-Secretase at a Novel Site" J Biol Chem 279(42):43419-43426 ( 2014).

(Continued)

Primary Examiner — Kahsay Habte
(74) Attorney, Agent, or Firm — Genentech, Inc.; Richard G. A. Bone

(57) ABSTRACT

The present invention relates to a compound of formula I, 1-1 or 1-2 wherein $R^1$ is hydrogen, lower alkyl, lower alkyl substituted by halogen, halogen, lower alkoxy, or lower alkoxy substituted by halogen; $R^1$ may be different if n=2 or 3 n is 1, 2 or 3 Ar is a six membered heteroaryl group, selected from wherein $R^2$ is hydrogen, lower alkyl, lower alkyl substituted by halogen, halogen or lower alkoxy; $R^3$ is hydrogen or halogen; or to a pharmaceutically active acid addition salt thereof. The compounds may be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

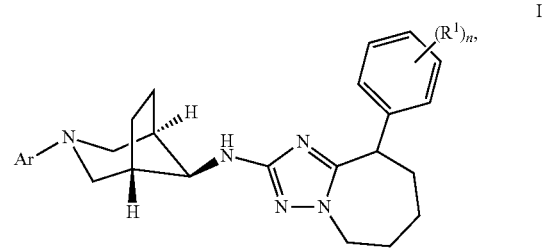

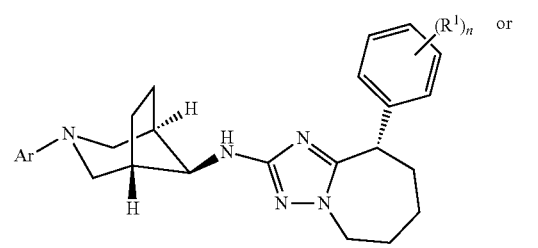

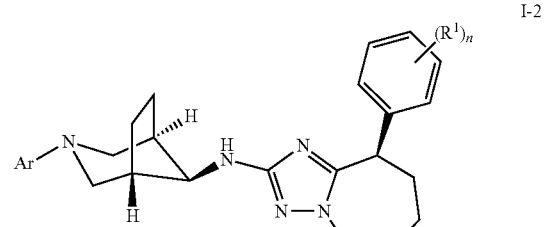

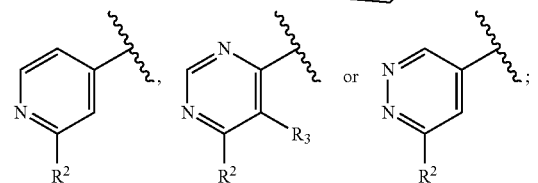

12 Claims, No Drawings

(58) Field of Classification Search
USPC .................................................. 514/214.02
See application file for complete search history.

(56) References Cited

OTHER PUBLICATIONS

Bursavich et al., "Gamma Secretase Modulators: New Alzheimer's Drugs on the Horizon?" Journal of Medicinal Chemistry 59:7389-7409 ( 2016).
Clarke et al., "Intra- or Intercomplex Binding to the g-Secretase Enzyme" Journal of Biological Chemistry 281(42):31279-31289 (Oct. 20, 2006).
Crump et al., "Development and Mechanism of γ-Secretase Modulators for Alzheimer's Disease" Biochemistry 52:3197-3216 ( 2013).
Ebke et al., "Novel g-Secretase Enzyme Modulators Directly Target Presenilin Protein*S" Journal of Biological Chemistry 286(43):37181-37186 (Oct. 28, 2011).
Hall et al., "Y-Secretase Modulators: Current Status and Future Directions" Progress in Medicinal Chemistry 53:101-145 ( 2014).
International Preliminary Report on Patentability (IPRP) for PCT/EP2017/077719 dated May 7, 2019.
International Search Report for PCT/EP2017/077719 dated Nov. 21, 2017.
Jantzen et al., "Microglial Activation and b-Amyloid Deposit Reduction Caused by a Nitric Oxide-Releasing Nonsteroidal Anti-Inflammatory Drug in Amyloid Precursor Protein Plus Presenilin-1 Transgenic Mice" Journal of Neuroscience 22:2246-2254 (Mar. 15, 2002).
Kukar et al., "Diverse compounds mimic Alzheimer disease-causing mutations by augmenting Ab42 production" Nature Medicine 11:545-550 (May 2005).
Lleo et al., "Nonsteroidal anti-inflammatory drugs lower Ab42 and change presenilin 1 conformation" Nature Medicine 10:1065-1066 (Oct. 2004).
Monihara et al., "Selective inhibition of Aβ42 production by NSAID R-enantiomers" Journal of Neurochemistry 83:1009-1012 (2002).
Narlawar et al., "Scaffold of the Cyclooxygenase-2 (COX-2) Inhibitor Carprofen Provides Alzheimer G-Seeretase Modulators" Journal of Medicinal Chemistry 49:7588-7591 ( 2006).
Oehlrich et al., "γ-Seeretase Modulators as Potential Disease Modifing Anti-Alzheimer's Drugs" Journal of Medicinal Chemistry 54:669-698 ( 2011).
Perretto et al., "Synthesis and biological activity of flurbiprofen analogues as elective inhibitors of B-amyloid $_{1-42}$ Secretion" J Med Chem 48:5705-5720 ( 2005).
Stock et al., "The geminal dimethyl analogue of Flurbiprofen as a novel Ab42 inhibitor and potential Alzheimer's disease modifying agent" Bioorganie & Medicinal Chemistry Letters 16:2219-2223 (2006).
Takahashi et al., "Sulindac Sulfide Is a Noncompetitive g-Secretase Inhibitor That Preferentially Reduces Ab42 Generation*" Journal of Biological Chemistry 278(20):18664-18670 ( 2003).
Weggen et al., "A subset of NSAIDs lower amyloidogenic Aβ42 independently of cyclooxygenase activity" Nature 414:212-216 (Nov. 8, 2001).

* cited by examiner

BICYCLIC HETEROARYL DERIVATIVES

CROSS-REFERENCE TO RELATED APPLICATIONS

This application is a National Stage Entry of PCT Application No. PCT/EP2017/077719, filed Oct. 30, 2017, which claims benefit of priority to European Application No. 16196720.3 filed Nov. 1, 2016, each of which is incorporated herein by reference in its entirety.

The present invention relates to a compound of formula I, I-1 or I-2,

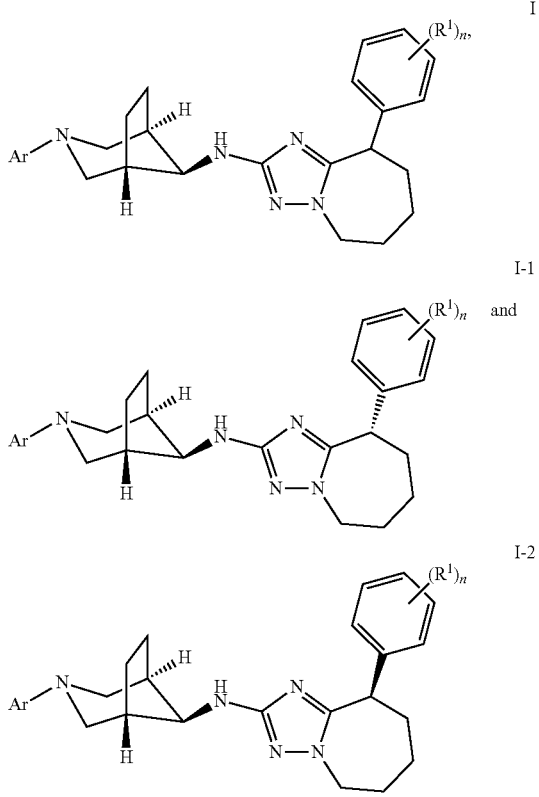

wherein
$R^1$ is hydrogen, lower alkyl, lower alkyl substituted by halogen, halogen, lower alkoxy, or lower alkoxy substituted by halogen;
$R^1$ may be different if n=2 or 3
n is 1, 2 or 3
Ar is a six membered heteroaryl group, selected from

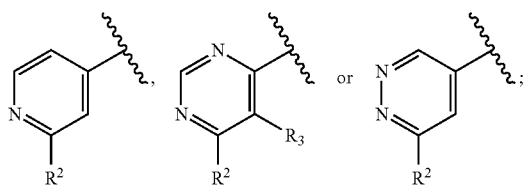

wherein
$R^2$ is hydrogen, lower alkyl, lower alkyl substituted by halogen, halogen or lower alkoxy;
$R^3$ is hydrogen or halogen;
or to a pharmaceutically active acid addition salt thereof.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, 525, pages 212-217. The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al., Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on γ-secretase modulation, for example the following publications:
Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Oehlich, Gijsen et al, J. Med. Chem., 54 (2011), 669-698
Li et al., Biochemistry, 52, (2013), 3197-3216
Hall et al, Progress in Med. Chem., 53 (2014) 101-145
Bursavich et al, J. Med. Chem., 59 (2016) DOI: 10.1021/acs.jmedchem.5b01960

The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$, and the like. The preferred group is $CF_3$.

The term "lower alkoxy" denotes a lower alkyl group as defined above, which group is connected via an O atom.

The term "lower alkoxy substituted by halogen" denotes a lower alkoxy group as defined above, wherein at least one hydrogen atom is replaced by halogen.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

One object of the present invention is a compound of formula IA, IA-1 or IA-2,

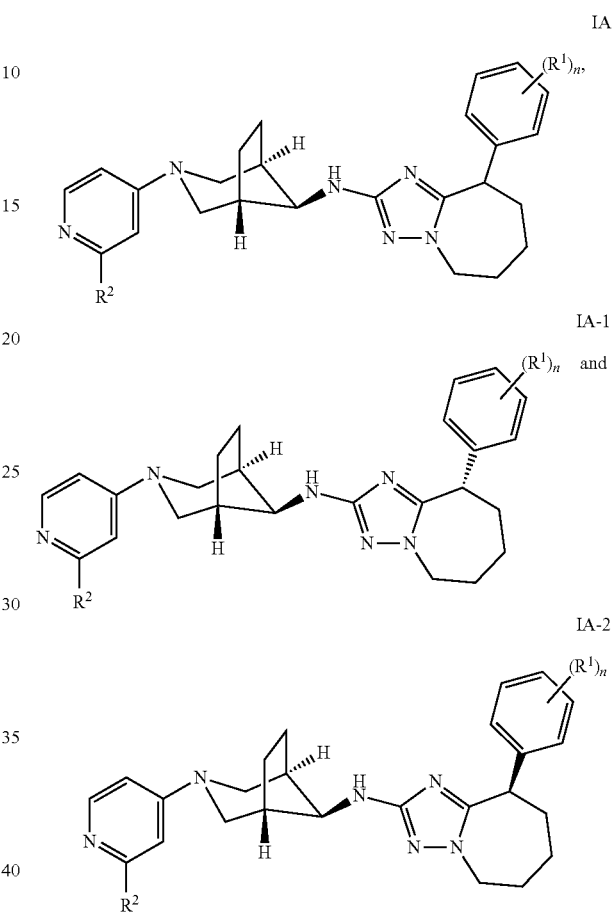

wherein
$R^1$ is hydrogen, lower alkyl, lower alkyl substituted by halogen, halogen, lower alkoxy, or lower alkoxy substituted by halogen;
$R^1$ may be different if n=2 or 3
n is 1, 2 or 3
$R^2$ is hydrogen, lower alkyl, lower alkyl substituted by halogen, halogen or lower alkoxy; or a pharmaceutically active acid addition salt thereof, for example the following compounds N-[(1R,5S,8S)-3-[2-(trifluoromethyl)-4-pyridyl]-3-azabicyclo[3.2.1]octan-8-yl]-9-(2,3,4-trifluorophenyl)-6,7,8,9-tetrahydro-5H-[1,2,4]triazolo[1,5-a]azepin-2-amine 9-[4-(trifluoromethyl)phenyl]-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine 9-(4-chlorophenyl)-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine 9-[3-(trifluoromethyl)phenyl]-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine N-[(1R,5S,8S)-3-(2-methoxy-4-pyridyl)-3-azabicyclo[3.2.1]octan-8-yl]-9-(2,3,4-trifluorophenyl)-6,7,8,9-tetrahydro-5H-[1,2,4]triazolo[1, 5-a]azepin-2-amine N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (9S)—N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine or (9R)—N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine.

One further object of the present invention is a compound of formula IB, IB-1 or IB-2,

IB

IB-1 and

IB-2 wherein
R¹ is hydrogen, lower alkyl, lower alkyl substituted by halogen, halogen, lower alkoxy, or lower alkoxy substituted by halogen;
R¹ may be different if n=2 or 3
n is 1, 2 or 3
R² is hydrogen, lower alkyl, lower alkyl substituted by halogen, halogen or lower alkoxy;
R³ is hydrogen or halogen;
or a pharmaceutically active acid addition salt thereof, for example the following compounds N-[(1R,5S,8S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine (9S)—N-[(1R,5S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine (9R)—N-[(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine 9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine (9S)-9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine (9R)-9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (9S)—N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (9R)—N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9S)—N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9R)—N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9S)—N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9R)—N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine N-[(1R,5S,8S)-3-(6-methoxypyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine N-[(1R,5S,8S)-3-(5-fluoro-6-methyl-pyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine 9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine (9S)-9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine or (9R)-9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine.

One object of the present invention is a compound of formula IC, IC-1 or IC-2,

IC

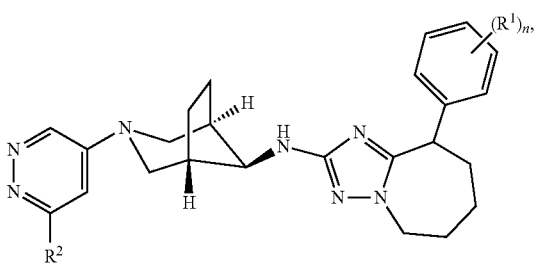

-continued

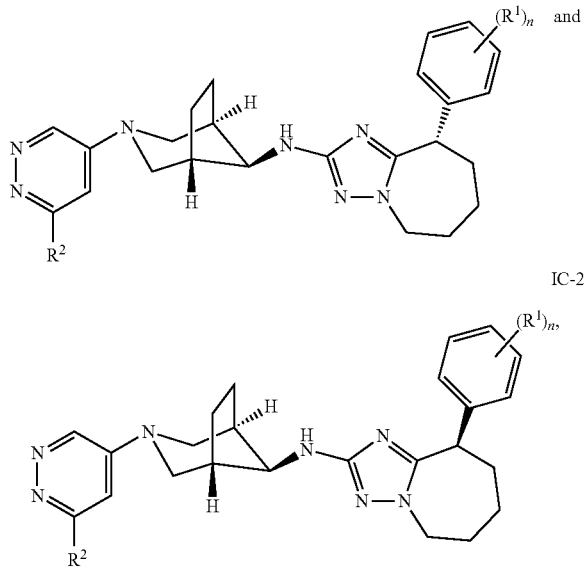

wherein
R¹ is hydrogen, lower alkyl, lower alkyl substituted by halogen, halogen, lower alkoxy, or lower alkoxy substituted by halogen;
R¹ may be different if n=2 or 3
n is 1, 2 or 3
R² is hydrogen, lower alkyl, lower alkyl substituted by halogen, halogen or lower alkoxy;
or a pharmaceutically active acid addition salt thereof, for example the following compounds N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9S)—N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9R)—N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9S)—N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9R)—N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9S)—N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (9R)—N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (9S)—N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (9R)—N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (9S)—N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine or (9R)—N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine.

The present compounds of formula I and their pharmaceutically acceptable salts can be prepared by methods known in the art, for example, by processes described below, which processes comprise
a) reacting a compound of formula 7

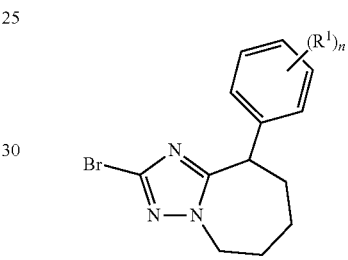

with a compound of formula 8

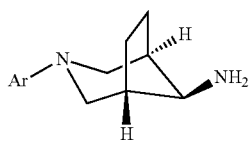

to a compound of formula I

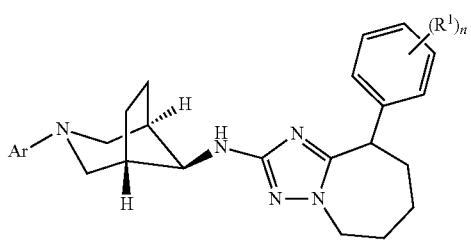

wherein the substituents have the meaning as described above, and, if desired, converting the compounds obtained into pharmaceutically acceptable acid addition salts; or b) cyclization of a compound of formula 14 with a compound of formula

Ar—X to a compound of formula I

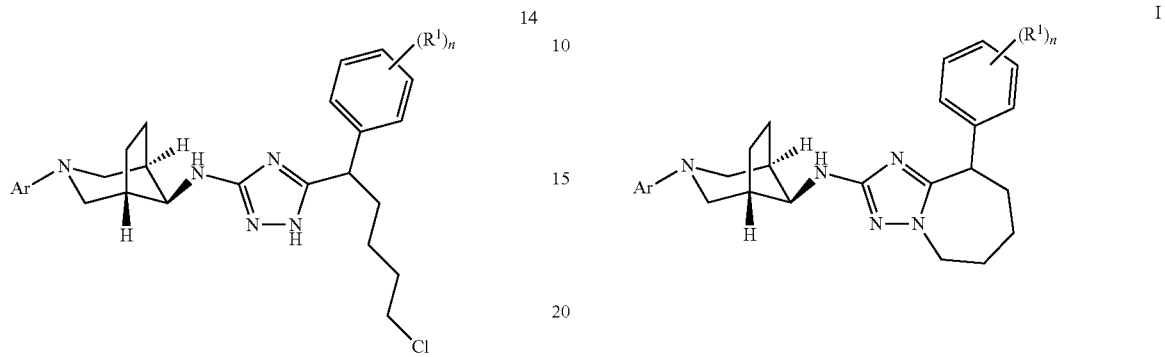

in the presence of KI and K$_2$CO$_3$ to a compound of formula I wherein the substituents have the meaning as described above, and X is halogen, and, if desired, converting the compounds obtained into pharmaceutically acceptable acid addition salts, or d) separating a racemic compound of formula I by a chiral HPLC separation to a compound of formulas I-1 or I-2.

In more detail, compounds of formula I and their intermediates may be prepared by schemes 1-5 and by the description of 43 specific examples.

General Synthesis for Compounds of Formula I

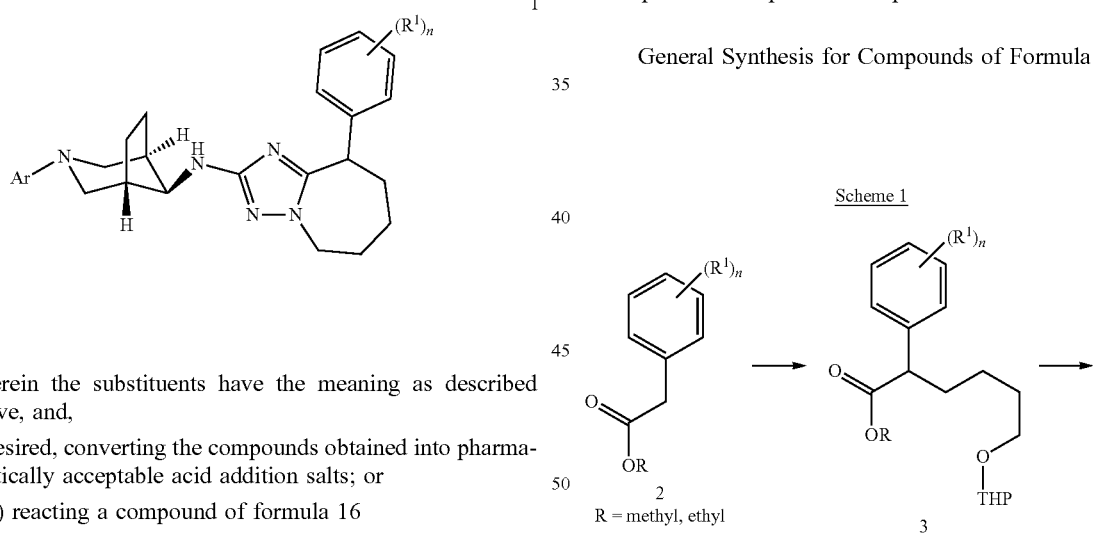

wherein the substituents have the meaning as described above, and, if desired, converting the compounds obtained into pharmaceutically acceptable acid addition salts; or c) reacting a compound of formula 16

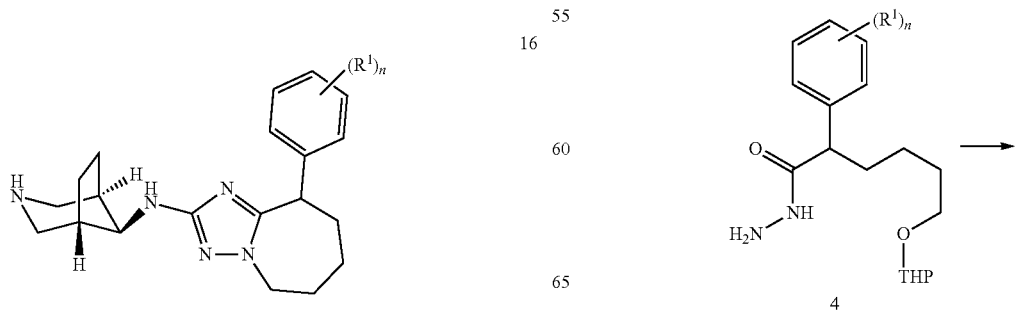

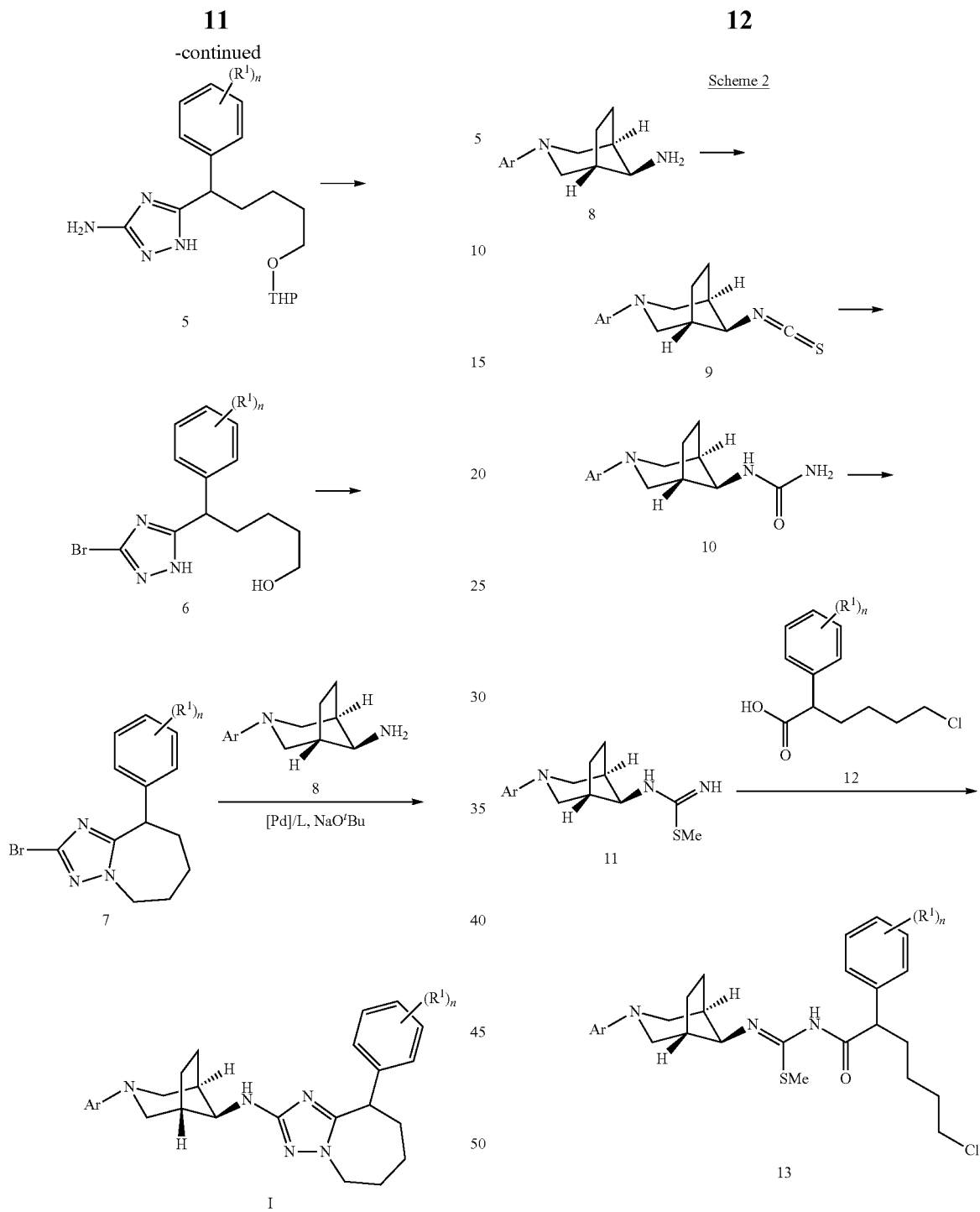

The preparation of derivatives of general formula I commenced by the alkylation of methyl or ethyl 2-phenylacetate 2 with 2-(4-bromobutoxy)tetrahydro-2H-pyran to yield 3 (scheme 1). Addition of hydrazine afforded the corresponding hydrazide 4. Upon reaction of 4 with 2-methyl-2-thiopseudourea sulfate was obtained the amino triazole 5. A Sandmeyer reaction afforded the corresponding deprotected Br-triazole derivative 6. An intramolecular cyclisation via a Mitsunobu reaction gave the versatile intermediates 7, which can easily undergo a Buchwald type reaction with different amines of type 8 affording final products of formula I.

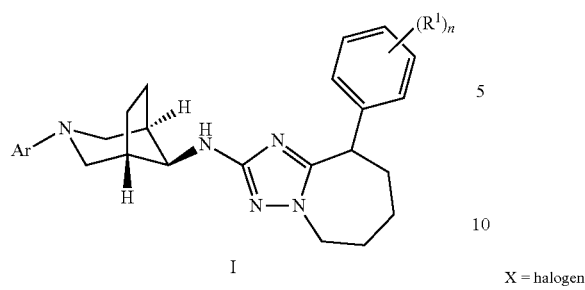

I

X = halogen

Alternatively, compounds of general formula I could be prepared in the following manner (scheme 2). The aminopiperidine 8 was converted into the corresponding isothiocyanato derivatives 9 upon reaction with 1,1'-thiocarbonyldipyridin-2(1H)-one. Addition of ammonia gave the thioureas 10 which can undergoes a S alkylation with MeI providing 11. An amid coupling with intermediates of formula 12 gave 13, which was readily converted into the triazole derivatives 14 upon reaction with hydrazine. Finally, an intramolecular cyclisation in the presence of KI and K₂CO₃ afforded compounds of formula I.

Alternatively, compounds of general formula I can be prepared as described in scheme 3. Intermediates 7 (describe in scheme 1) could undergo a Buchwald type coupling with a commercially available amino piperidine derivative to form 15. Boc-deprotection under standard conditions gave 16. The coupling of 16 with heterocyclic halides of general formula Ar—X can be accomplished under thermal conditions in a solvent such as ethanol or NMP in the presence of a base such as Et₃N or by using displacement reactions under catalytic conditions (like e.g. palladium(0) or copper (II) catalysis) to provide compounds of formula I.

General Synthesis of Intermediates 8

Scheme 3

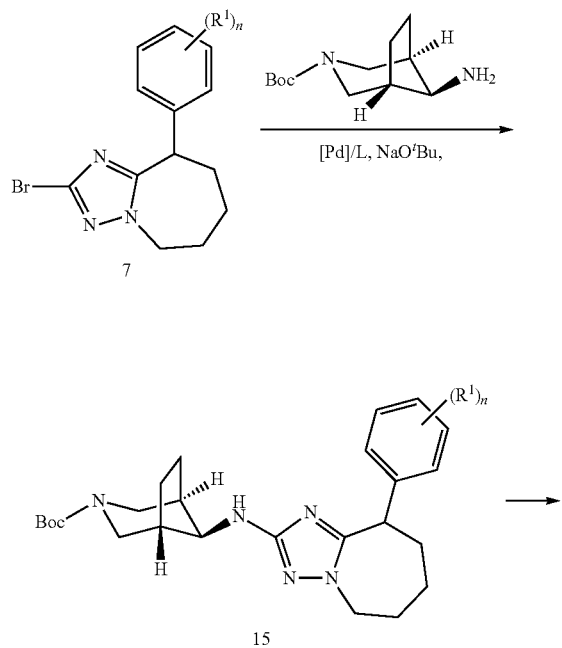

Scheme 4

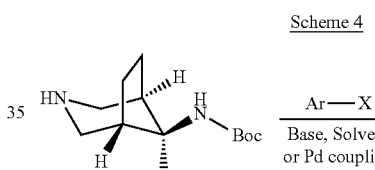

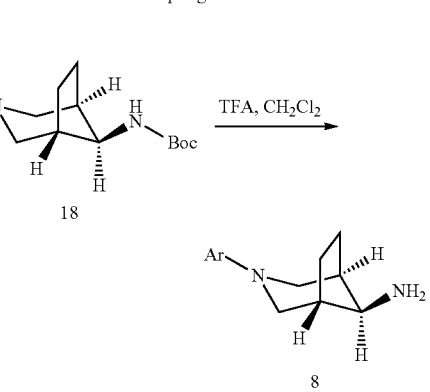

Compounds of formula 8 used in schemes 1-2 can be prepared according to the scheme 4, starting from tert-butyl N-[(1S,5R,8S)-3-azabicyclo[3.2.1]octan-8-yl]carbamate 17 (CAS 847862-26-4). The coupling of 17 with heterocyclic halides of general formula Ar—X can be accomplished under thermal conditions in a solvent such as ethanol or NMP in the presence of a base such as Et₃N or by using displacement reactions under catalytic conditions (like e.g. palladium(0) or copper(II) catalysis) to provide compounds of formula 18. After deprotection with acid e.g. trifluoro acetic acid compounds of formula 8 were obtained.

The heterocycles halides are either commercial available, known in the literature so they can be prepared by methods known in the art.

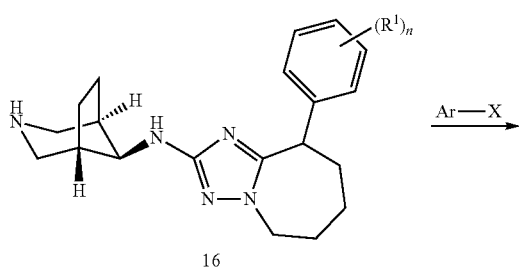

General Synthesis of Intermediates 12

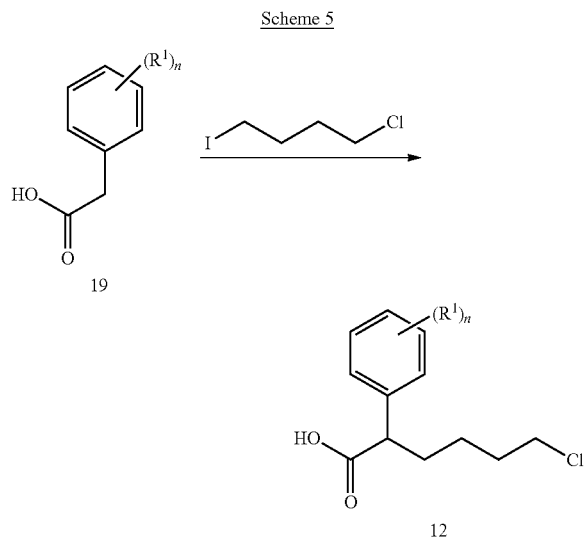

Scheme 5

Intermediates 12 were readily prepared upon alkylation of commercially available acids 19 with 1-chloro-4-iodo-butane in the presence of a base (e.g. NaHMDS) at low temperature.

The heterocycles halides are either commercial available, known in the literature so they can be prepared by methods known in the art or alternatively could be prepared as described in the specification.

The compounds were investigated in accordance with the test given hereinafter.

Description of γ-Secretase Assay

Cellular γ-Secretase Assay

Human neuroglioma H4 cells overexpressing human APP695 with the Swedish double mutation (K595N/M596L) were plated at 30,000 cells/well/100 al in 96-well plates in IMDM media containing 10% FCS, 0.2 mg/l Hygromycin B and incubated at 37° C., 5% $CO_2$.

3-4 hr post plating, compounds are a diluted in media and 50 µl is added as 1.5-fold concentrate to achieve the final concentration. Compound incubation is performed for 24 hr. Final doses typically range from 4 µM down to 0.0013 µM in half-log steps resulting in a eight point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat #AL203C, Perkin Elmer). 20 µl of the cell culture supernatant was transferred to an assay plate. Then 10 µl of a mixture of the AlphaLisa coupled capture antibody and the biotinylated detection antibody was added and incubated for 3 hours at room temperature while softly shaking the assay plate. After a further addition of 20 µl of the Donor beads the assay plate was incubated for 30 min at room temperature and constant shaking without exposure to direct light. The assay plate was then read on a Paradigm AlphaLisa Reader using the build-in program with excitation at 680 nm and emission at 570 nm.

The measured signals were then used to calculate $IC_{50}$ values for inhibition of Aβ42 secretion by nonlinear regression fit analysis using XLfit 5.3 software (IDBS).

The table below shows the data for all compounds for the inhibition of Aβ42 secretion (nM):

| Example No. | $EC_{50}$ Aβ42 (uM) | Example No. | $EC_{50}$ Aβ42 (nM) |
|---|---|---|---|
| 1 | 0.0346 | 23 | 0.0125 |
| 2 | 0.0484 | 24 | 0.0077 |
| 3 | 0.0206 | 25 | 0.0134 |
| 4 | 0.0374 | 26 | 0.0260 |
| 5 | 0.0116 | 27 | 0.0265 |
| 6 | 0.0506 | 28 | 0.0201 |
| 7 | 0.0234 | 29 | 0.0160 |
| 8 | 0.0319 | 30 | 0.0136 |
| 9 | 0.0489 | 31 | 0.0151 |
| 10 | 0.0337 | 32 | 0.0334 |
| 11 | 0.0280 | 33 | 0.0232 |
| 12 | 0.0149 | 34 | 0.0256 |
| 13 | 0.0150 | 35 | 0.0326 |
| 14 | 0.0126 | 36 | 0.0148 |
| 15 | 0.0084 | 37 | 0.0230 |
| 16 | 0.0071 | 38 | 0.0262 |
| 17 | 0.0177 | 39 | 0.0155 |
| 18 | 0.0124 | 40 | 0.0120 |
| 19 | 0.0125 | 41 | 0.0202 |
| 20 | 0.0085 | 42 | 0.0231 |
| 21 | 0.0534 | 43 | 0.0214 |
| 22 | 0.0303 | | |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL PART

The following examples are provided for illustration of the invention. They should not be considered as limiting the scope of the invention, but merely as being representative thereof.

General
Analytical Methods
HPLC (method LCMS_fastgradient)
Column: Agilent Zorbax Eclipse Plus C18, Rapid Resolution HT, 2.1×30 mm, 1.8 μm, Part. no. 959731-902
Solvent A: Water 0.01% Formic Acid; Solvent B: acetonitrile (MeCN) Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

Abbreviations

The following abbreviations were used in the experimental part:
THF=tetrahydrofurane;
TBME=methyl-tert-butylether;
DMF=dimethylformamide;
TLC=thin layer chromatography;
RT=room temperature, 20-25° C.
THP=tetrahydro-pyran

PREPARATION OF INTERMEDIATES

Intermediates of Type 8

Intermediate 8-1

(1R,5S,8S)-3-(6-methylpyrimidin-4-yl)-3-azabicyclo[3.2.1]octan-8-amine

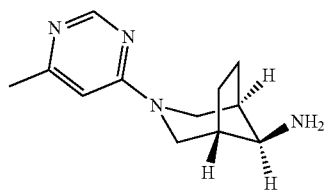 [SMILES: Cc1cc(N2C[C@H]3CC[C@@H](C2)[C@@H]3N)ncn1]

Step 1:
In a sealed tube tert-butyl N-[(1R,5S,8S)-3-azabicyclo[3.2.1]octan-8-yl]carbamate (500 mg, 2.21 mmol) was dissolved in EtOH (10 mL) and 4-chloro-6-methylpyrimidine (869 mg, 6.63 mmol) was added followed by triethylamine (894 mg, 1.23 mL, 8.84 mmol). The reaction mixture was stirred at 130° C. overnight. The crude reaction mixture was concentrated in vacuum. The residue was diluted with 20 mL of CH$_2$Cl$_2$ and 20 mL of water. The organic phase was extracted with CH$_2$Cl$_2$ (3×20 mL), dried over MgSO$_4$ and concentrated in vacuum. The crude material was purified by flash chromatography (0% to 100% EtOAc in heptane) to afford tert-butyl N-[(1R,5S,8S)-3-(6-methylpyrimidin-4-yl)-3-azabicyclo[3.2.1]octan-8-yl]carbamate as a yellow solid (496 mg, 71% yield). MS (ES+) m/z: 319.2 [(M+H)$^+$]
Step 2:
To a light yellow solution of tert-butyl N-[(1R,5S,8S)-3-(6-methylpyrimidin-4-yl)-3-azabicyclo[3.2.1]octan-8-yl]carbamate (260 mg, 817 μmol) in CH$_2$Cl$_2$ (8 mL) was added TFA (931 mg, 629 µl, 8.17 mmol). The reaction mixture was stirred at room temperature over night and concentrated in vacuum. The crude material was purified by Ion-exchange column (Si-SCX-2, 10 g, washed with MeOH and liberated with MeOH (NH$_3$ 2M)) to afford (1R,5S,8S)-3-(6-methylpyrimidin-4-yl)-3-azabicyclo[3.2.1]octan-8-amine 8-1 (195 mg, 804 µmol, 98.5% yield) that was used in the next step without further purification. MS (ES+) m/z: 219.2 [(M+H)$^+$].

Intermediate 8-2

(1R,5S,8S)-3-(5-fluoro-6-methyl-pyrimidin-4-yl)-3-azabicyclo[3.2]octan-8-amine

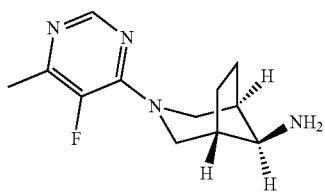 [SMILES: Cc1ncnc(N2C[C@H]3CC[C@@H](C2)[C@@H]3N)c1F]

Step 1:
In analogy to the preparation of the intermediate 8-1 (step 1) from tert-butyl N-[(1R,5S,8S)-3-azabicyclo[3.2.1]octan-8-yl]carbamate (200 mg, 884 µmol) and 4-chloro-5-fluoro-6-methylpyrimidine (194 mg, 1.33 mmol) in a sealed tube at 100° C. and EtOH as solvent in the presence of triethylamine (358 mg, 493 µl, 3.53 mmol), tert-butyl N-[(1R,5S,8S)-3-(5-fluoro-6-methyl-pyrimidin-4-yl)-3-azabicyclo[3.2.1]octan-8-yl]carbamate was obtained as a white solid (255 mg, 758 µmol, 86% yield). MS (ES+) m/z: 337.3 [(M+H)$^+$].

Step 2:
In analogy to the preparation of intermediate 8-1 (step 2) from tert-butyl N-[(1R,5S,8S)-3-(5-fluoro-6-methyl-pyrimidin-4-yl)-3-azabicyclo[3.2.1]octan-8-yl]carbamate (253 mg, 752 mol) in CH$_2$Cl$_2$ in the presence of aqueous HCl 37% (445 mg, 371 µl, 4.51 mmol), (1R,5S,8S)-3-(5-fluoro-6-methyl-pyrimidin-4-yl)-3-azabicyclo[3.2.1]octan-8-amine (170 mg, 719 µmol, 96% yield) was obtained as a white solid and used directly in the next step without further purification. MS (ES+) m/z: 237.1 [(M+H)$^+$].

Intermediate 8-3

(1R,5S,8S)-3-(6-chloropyrimidin-4-yl)-3-azabicyclo[3.2.1]octan-8-amine

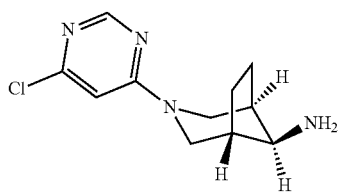 [SMILES: N[C@@H]1[C@@H]2CC[C@H]1CN(c1cc(Cl)ncn1)C2]

Step 1:
In analogy to the preparation of the intermediate 8-1 (step 1) from tert-butyl N-[(1R,5S,8S)-3-azabicyclo[3.2.1]octan-8-yl]carbamate (250 mg, 1.1 mmol) and 4-chloro-6-fluoro-pyrimidine (220 mg, 1.66 mmol) in a sealed tube at 100° C. using EtOH as solvent in the presence of triethylamine (447 mg, 616 µl, 4.42 mmol), tert-butyl N-[(1R,5S,8S)-3-(6-chloropyrimidin-4-yl)-3-azabicyclo[3.2.1]octan-8-yl]carbamate (329 mg, 88% yield) was obtained as a white solid. MS (ES+) m/z: 339.2 [(M+H)$^+$].

Step 2:
In analogy to the preparation of intermediate 8-1 (step 2) from tert-butyl N-[(1R,5S,8S)-3-(6-chloropyrimidin-4-yl)-3-azabicyclo[3.2.1]octan-8-yl]carbamate (325 mg, 959 µmol) in CH$_2$Cl$_2$ in the presence of HCl 37% (567 mg, 473 µl, 5.76 mmol), (1R,5S,8S)-3-(6-chloropyrimidin-4-yl)-3-azabicyclo[3.2.1]octan-8-amine (230 mg, 100% yield) was obtained as a white solid and used directly in the next step without further purification. MS (ES+) m/z: 239.2 [(M+H)$^+$].

Intermediate 8-4

(1R,5S,8S)-3-(6-methoxypyrimidin-4-yl)-3-azabicyclo[3.2.1]octan-8-amine

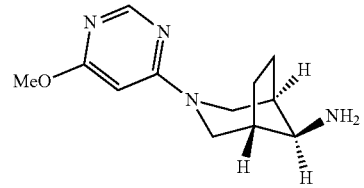 [SMILES: COc1cc(N2C[C@H]3CC[C@@H](C2)[C@@H]3N)ncn1]

Step 1:
In analogy to the preparation of the intermediate 8-1 (step 1) from tert-butyl N-[(1R,5S,8S)-3-azabicyclo[3.2.1]octan-8-yl]carbamate (250 mg, 1.1 mmol) and 4-iodo-6-methoxy-pyrimidine (391 mg, 1.66 mmol) in a sealed tube at 100° C. using DMF as solvent in the presence of K$_2$CO$_3$ (458 mg, 3.31 mmol), tert-butyl N-[(1R,5S,8S)-3-(6-methoxypyrimidin-4-yl)-3-azabicyclo[3.2.1]octan-8-yl]carbamate (315 mg, 85% yield) was obtained as a white solid. MS (ES+) m/z: 335.2 [(M+H)$^+$].

Step 2:
In analogy to the preparation of intermediate 8-1 (step 2) from tert-butyl N-[(1R,5S,8S)-3-(6-methoxypyrimidin-4-yl)-3-azabicyclo[3.2.1]octan-8-yl]carbamate (330 mg, 987 µmol) in CH$_2$Cl$_2$ in the presence of TFA (1.13 g, 760 al, 9.87 mmol), (1R,5S,8S)-3-(6-methoxypyrimidin-4-yl)-3-azabicyclo[3.2.1]octan-8-amine (222 mg, 96% yield) was obtained as a white solid and used directly in the next step without further purification. MS (ES+) m/z: 235.2 [(M+H)$^+$].

Intermediate 8-5

(1R,5S,8S)-3-[2-(trifluoromethyl)-4-pyridyl]-3-azabicyclo[3.2.1]octan-8-amine

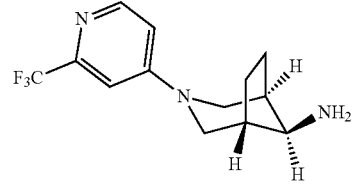 [SMILES: N[C@@H]1[C@@H]2CC[C@H]1CN(c1ccnc(C(F)(F)F)c1)C2]

Step 1:

In analogy to the preparation of the intermediate 8-1 (step 1) from tert-butyl N-[(1R,5S,8S)-3-azabicyclo[3.2.1]octan-8-yl]carbamate (1.57 g, 6.87 mmol) and 4-iodo-2-(trifluoromethyl)pyridine (1.5 g, 5.33 mmol) in a sealed tube at 150° C. using NMP as solvent in the presence of DIPEA (964 mg, 1.3 ml, 7.46 mmol), tert-butyl N-[(1R,5S,8S)-3-[2-(trifluoromethyl)-4-pyridyl]-3-azabicyclo[3.2.1]octan-8-yl]carbamate (1.37 g, 70% yield) was obtained as a white solid. MS (ES+) m/z: 372.2 [(M+H)+].

Step 2:

In analogy to the preparation of intermediate 8-1 (step 2) from tert-butyl N-[(1R,5S,8S)-3-[2-(trifluoromethyl)-4-pyridyl]-3-azabicyclo[3.2.1]octan-8-yl]carbamate (1.05 g, 2.82 mmol) in CH$_2$Cl$_2$ in the presence of HCl 37% (1.68 g, 1.4 mL, 17 mmol), (1R,5S,8S)-3-[2-(trifluoromethyl)-4-pyridyl]-3-azabicyclo[3.2.1]octan-8-amine (735 mg, 96% yield) was obtained as a white solid and used directly in the next step without further purification. MS (ES+) m/z: 272.2 [(M+H)+].

Intermediate 8-6

(1R,5S,8S)-3-(2-methoxy-4-pyridyl)-3-azabicyclo[3.2.1]octan-8-amine

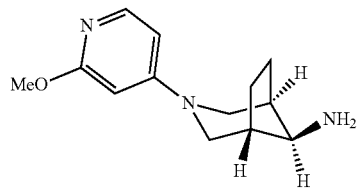 [SMILES: COc1cc(N2C[C@H]3CC[C@@H](C2)[C@@H]3N)ccn1]

Step 1:

In analogy to the preparation of the intermediate 8-1 (step 1) from tert-butyl N-[(1R,5S,8S)-3-azabicyclo[3.2.1]octan-8-yl]carbamate (2.00 g, 8.84 mmol) and 4-fluoro-2-methoxypyridine (1.12 g, 8.84 mmol) in a sealed tube at 140° C. using NMP as solvent in the presence of DIPEA (2.28 g, 3.09 mL, 17.70 mmol), tert-butyl N-[(1R,5S,8S)-3-(2-methoxy-4-pyridyl)-3-azabicyclo[3.2.1]octan-8-yl]carbamate (1.42 g, 48%) was obtained as a white solid. MS (ES+) m/z: 334.3 [(M+H)+].

Step 2:

In analogy to the preparation of intermediate 8-1 (step 2) from tert-butyl N-[(1R,5S,8S)-3-(2-methoxy-4-pyridyl)-3-azabicyclo[3.2.1]octan-8-yl]carbamate (1.42 g, 4.26 mmol) in CH$_2$Cl$_2$ in the presence of TFA (7.38 g, 5.0 mL, 15.2 mmol), (1R,5S,8S)-3-(2-methoxy-4-pyridyl)-3-azabicyclo[3.2.1]octan-8-amine (0.89 g, 89%) was obtained as a white solid and used directly in the next step without further purification. MS (ES+) m/z: 234.2 [(M+H)+].

Intermediate 8-7

(1R,5S,8S)-3-(6-chloropyridazin-4-yl)-3-azabicyclo[3.2.1]octan-8-amine

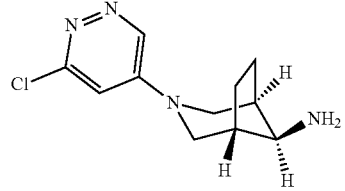 [SMILES: N[C@@H]1[C@@H]2CC[C@H]1CN(c1cnnc(Cl)c1)C2]

Step 1:

In analogy to the preparation of the intermediate 8-1 (step 1) from tert-butyl N-[(1R,5S,8S)-3-azabicyclo[3.2.1]octan-8-yl]carbamate (2.00 g, 8.84 mmol) and 3,5-dichloropyridazine (2.0 g, 13.4 mmol) in a sealed tube at 90° C. using EtOH as solvent in the presence of Et$_3$N (3.63 g, 5.0 mL, 35.9 mmol), tert-butyl N-[(1R,5S,8S)-3-(6-chloropyridazin-4-yl)-3-azabicyclo[3.2.1]octan-8-yl]carbamate (1.71 g, 54%) was obtained as a white solid. MS (ES+) m/z: 339.2 [(M+H)+].

Step 2:

In analogy to the preparation of intermediate 8-1 (step 2) from tert-butyl N-[(1R,5S,8S)-3-(6-chloropyridazin-4-yl)-3-azabicyclo[3.2.1]octan-8-yl]carbamate (0.93 g, 2.72 mmol) in CH$_2$Cl$_2$ in the presence of HCl 37% (1.61 g, 1.34 mL, 16.3 mmol), (1R,5S,8S)-3-(6-chloropyridazin-4-yl)-3-azabicyclo[3.2.1]octan-8-amine (0.65 g, 100%) was obtained as a white solid and used directly in the next step without further purification. MS (ES+) m/z: 239.1 [(M+H)+].

Intermediate 8-8

(1R,5S,8S)-3-(6-methoxypyridazin-4-yl)-3-azabicyclo[3.2.1]octan-8-amine

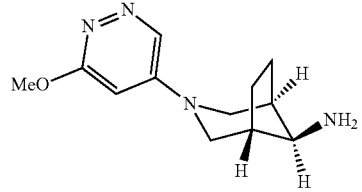 [SMILES: COc1cc(N2C[C@H]3CC[C@@H](C2)[C@@H]3N)cnn1]

Step 1:

To a solution of tert-butyl N-[(1R,5S,8S)-3-(6-chloropyridazin-4-yl)-3-azabicyclo[3.2.1]octan-8-yl]carbamate (963 mg, 2.70 mmol) in MeOH (22 mL) in a sealed tube was added a methanol solution of NaOMe (25%, 1.9 mL, 8.3 mmol). The reaction mixture was heated at 85° C. over night. The reaction mixture was adsorbed on Isolute HM-N and a column chromatography gave tert-butyl N-[(1R,5S,8S)-3-(6-methoxypyridazin-4-yl)-3-azabicyclo[3.2.1]octan-8-yl]carbamate (362 mg, 38%) as a white solid. MS (ES+) m/z: 335.2 [(M+H)+].

Step 2:

In analogy to the preparation of intermediate 8-1 (step 2) from tert-butyl N-[(1R,5S,8S)-3-(6-methoxypyridazin-4- yl)-3-azabicyclo[3.2.1]octan-8-yl]carbamate (0.93 g, 2.72 mmol) in CH$_2$Cl$_2$ in the presence of TFA (1.12 g, 0.76 mL, 9.86 mmol), (1R,5S,8S)-3-(6-methoxypyridazin-4-yl)-3-azabicyclo[3.2.1]octan-8-amine (225 mg, 96%) was obtained as a white solid and used directly in the next step without further purification. MS (ES+) m/z: 235.2 [(M+H)$^+$].

Intermediates of Type 12

Intermediate 12-1

6-chloro-2-(2,3,4-trifluorophenyl)hexanoic acid

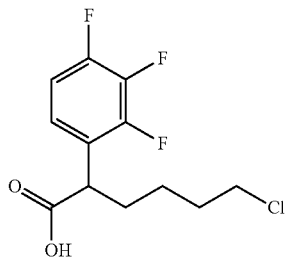 [SMILES: O=C(O)C(CCCCCl)c1ccc(F)c(F)c1F]

To a solution of 2-(2,3,4-trifluorophenyl)acetic acid (2 mmol) in toluene (3 mL) at −45° C. was added NaHMDS 1M in THF (4.2 mmol). The reaction was stirred at this temperature for 1 hour before being cannulated into a solution of 1-chloro-4-iodobutane (2.2 mmol) in toluene also at −45° C. The resulting reaction mixture was then warmed to RT slowly over one hour and stirred an other 30 minutes. HCl 2M was added until pH=1, and the product was extracted with EtOAc. The organic phase was dried over Na$_2$SO$_4$, filtered and concentrated under vacuo. Column chromatography (SiO$_2$, CH$_2$Cl$_2$/MeOH) afforded the title product (29%) as a colorless oil. MS (ES+) m/z: 279.2 [(M−H)$^+$].

Intermediate 12-2

6-chloro-2-[4-(trifluoromethyl)phenyl]hexanoic acid

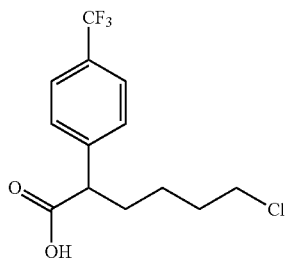

With a similar method as for the preparation of intermediate 12-1, from 2-[4-(trifluoromethyl)phenyl] acetic acid was prepared the title compound as a waxy solid. MS (ES+) m/z: 293.1 [(M−H)$^+$].

Intermediate 12-3

6-chloro-2-(4-chlorophenyl)hexanoic acid

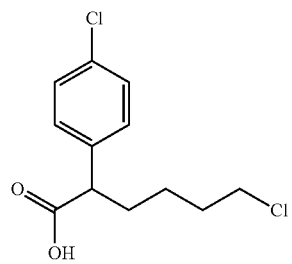 [SMILES: O=C(O)C(CCCCCl)c1ccc(Cl)cc1]

With a similar method as for the preparation of intermediate 12-1, from 2-(4-chlorophenyl)acetic acid was prepared the title compound as a solid. MS (ES+) m/z: 260.1 [(M−H)$^+$].

Intermediate 12-4

6-chloro-2-[3-(trifluoromethyl)phenyl]hexanoic acid

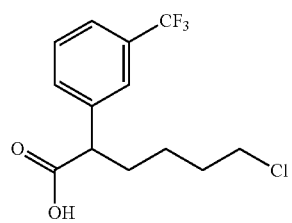 [SMILES: O=C(O)C(CCCCCl)c1cccc(C(F)(F)F)c1]

With a similar method as for the preparation of intermediate 12-1, from 2-[3-(trifluoromethyl)phenyl]acetic acid was prepared the title compound as a light yellow oil. MS (ES+) m/z: 293.1 [(M−H)$^+$].

Intermediate 12-5

6-chloro-2-(3,4-difluorophenyl)hexanoic acid

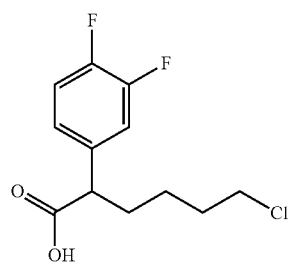 [SMILES: O=C(O)C(CCCCCl)c1ccc(F)c(F)c1]

With a similar method as for the preparation of intermediate 12-1, from 2-(3,4-difluorophenyl)acetic acid was prepared the title compound as a light yellow oil. MS (ES+) m/z: 261.8 [(M−H)$^+$].

General Procedure 1: Buchwald Coupling Reaction

To a solution of an intermediate 7, in 1,4-dioxane was added 1.1 equivalent of an intermediate 8 or of the commercially available tert-butyl (1R,5S)-8-amino-3-azabicyclo[3.2.1]octane-3-carboxylate. The reaction mixture was degased and a palladium catalyst [either dibromo-bis-(tri-tert.-butyl)-phosphine-palladium (0.1 eq. CAS185812-86-6) or tri(dibenzylidenacetonne) dipalladium(0) CAS51364-51-3 in the presence of 2-di-tert-butylphosphino-2',4',6'-triisopropylbiphenyl CAS564483-19-8] and NaOtBu (2.1 eq.) were added. The reaction mixture was heated at 100° C. until completion of the reaction (usually between 2 and 8 hours) and concentrated under vacuo. A purification was done either by column chromatography or reverse phase preparative HPLC to afford the desired product.

Example 1

N-[(1R,5S,8S)-3-[2-(trifluoromethyl)-4-pyridyl]-3-azabicyclo[3.2.1]octan-8-yl]-9-(2,3,4-trifluorophenyl)-6,7,8,9-tetrahydro-5H-[1,2,4]triazolo[1,5-a]azepin-2-amine

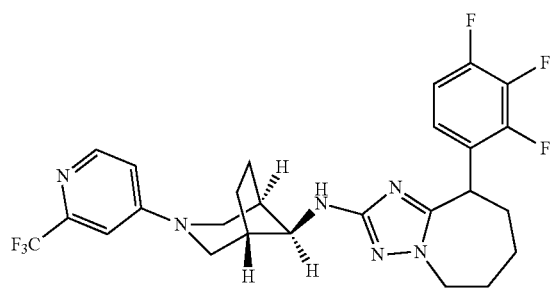 [SMILES: Fc1ccc(C2CCCCn3nc(N[C@@H]4[C@@H]5CC[C@H]4CN(c4ccnc(C(F)(F)F)c4)C5)nc32)c(F)c1F]

Step 1: (1R,5S,8S)-8-isothiocyanato-3-[2-(trifluoromethyl)-4-pyridyl]-3-azabicyclo[3.2.1]octane

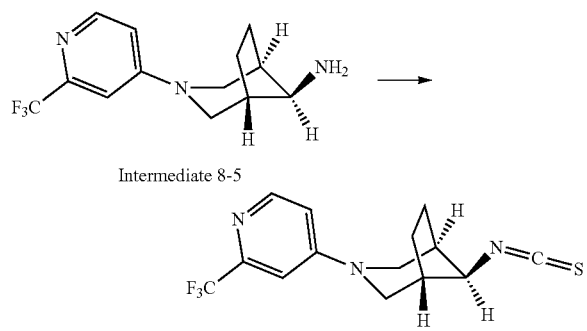

Intermediate 8-5

To a solution of (1R,5S,8S)-3-[2-(trifluoromethyl)-4-pyridyl]-3-azabicyclo[3.2.1]octan-8-amine (intermediate 8-5) (250 mg, 0.92 mmol) in CH$_2$Cl$_2$ (3.5 mL) was added 1-(2-oxopyridine-1-carbothioyl)pyridin-2-one and NEt(iPr)$_2$ (0.16 mL, 0.92 mmol). The reaction mixture was stirred at RT over night, concentrated under vacuo and a column chromatography (SiO$_2$, Heptane/EtOAc) afforded 240 mg (83%) of (1R,5S,8S)-8-isothiocyanato-3-[2-(trifluoromethyl)-4-pyridyl]-3-azabicyclo[3.2.1]octane as a yellow solid. MS (ES+) m/z: 314.2 [(M+H)$^+$].

Step 2: [(1R,5S,8S)-3-[2-(trifluoromethyl)-4-pyridyl]-3-azabicyclo[3.2.1]octan-8-yl]thiourea

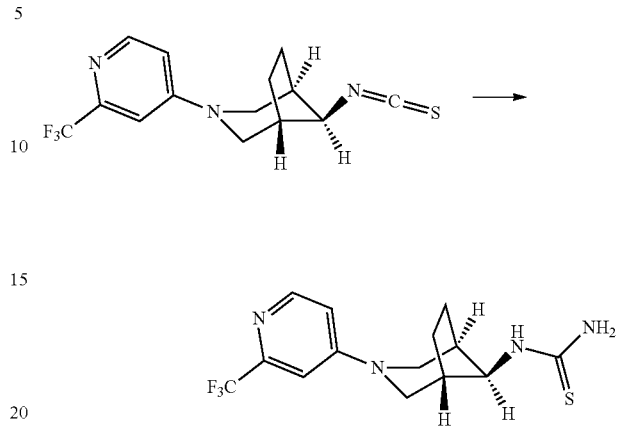

To a solution of ammonia 7N in MeOH (2.1 mL, 15.1 mmol) was added (1R,5S,8S)-8-isothiocyanato-3-[2-(trifluoromethyl)-4-pyridyl]-3-azabicyclo[3.2.1]octane (237 mg, 0.75 mmol). The reaction mixture was stirred at RT for one hour. The newly formed precipitate was collected by filtration and washed with cold MeOH and dried under vacuo to afford 200 mg (80%) of [(1R,5S,8S)-3-[2-(trifluoromethyl)-4-pyridyl]-3-azabicyclo[3.2.1]octan-8-yl]thiourea as a white solid. MS (ES+) m/z: 331.2 [(M+H)$^+$].

Step 3: 2-methyl-3-[(1R,5S,8S)-3-[2-(trifluoromethyl)-4-pyridyl]-3-azabicyclo[3.2.1]octan-8-yl]isothiourea hydroiodide

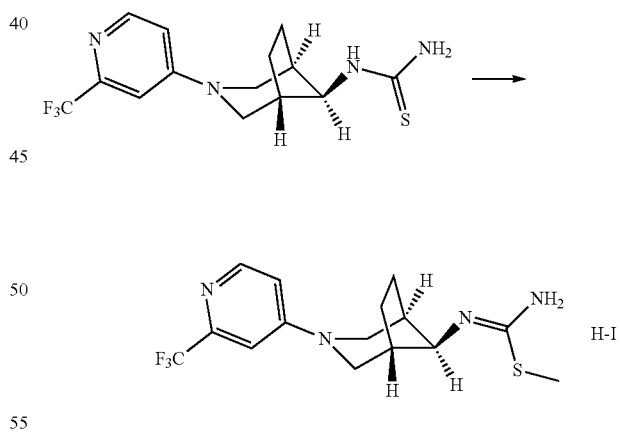

In a sealed tube, to a solution of [(1R,5S,8S)-3-[2-(trifluoromethyl)-4-pyridyl]-3-azabicyclo[3.2.1]octan-8-yl]thiourea (196 mg, 0.59 mmol) in EtOH (2 mL) was added MeI (40 µL, 0.65 mmol). The reaction mixture was heated at 80° C. for three hours. The reaction mixture was concentrated under under vacuo ad the resulting solid was triturated in Et$_2$O, the product collected by filtration and dried under vacuo to afford 246 mg (88%) of 2-methyl-3-[(1R,5S,8S)-3-[2-(trifluoromethyl)-4-pyridyl]-3-azabicyclo[3.2.1]octan-8-yl]isothiourea hydroiodide as a white solid. MS (ES+) m/z: 345.2 [(M+H)$^+$].

Step 4: 6-chloro-N—[(Z)—C-methylsulfanyl-N-[(1R,5S,8S)-3-[2-(trifluoromethyl)-4-pyridyl]-3-azabicyclo[3.2.1]octan-8-yl]carbonimidoyl]-2-(2,3,4-trifluorophenyl)hexanamide

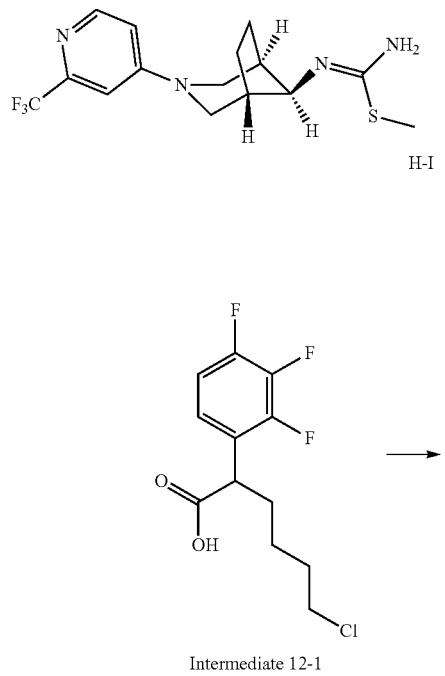

To a solution of 2-methyl-3-[(1R,5S,8S)-3-[2-(trifluoromethyl)-4-pyridyl]-3-azabicyclo[3.2.1]octan-8-yl]isothiourea hydroiodide (136 mg, 0.29 mmol) in DMF (2 mL) was added 6-chloro-2-(2,3,4-trifluorophenyl)hexanoic acid (100 mg, 0.29 mmol), HOBt (133 mg, 0.86 mmol), EDC.HCl (166 mg, 0.86 mmol) and NEt(iPr)$_2$ (0.40 mL, 2.31 mmol). The reaction mixture was stirred at RT for five hours and then poured into water. The product was extracted with EtOAc three times, and the combined organic phase was dried over Na$_2$SO$_4$, and concentrated under vacuo. A column chromatography (SiO$_2$, Heptane/EtOAc) gave 175 mg (54%) of 6-chloro-N—[(Z)—C-methylsulfanyl-N-[(1R,5S,8S)-3-[2-(trifluoromethyl)-4-pyridyl]-3-azabicyclo[3.2.1]octan-8-yl]carbonimidoyl]-2-(2,3,4-trifluorophenyl)hexanamide as a light yellow oil. MS (ES+) m/z: 607.3 [(M+H)$^+$].

Step 5: (1S,5R,8S)—N-[5-[5-chloro-1-(2,3,4-trifluorophenyl)pentyl]-4H-1,2,4-triazol-3-yl]-3-[2-(trifluoromethyl)-4-pyridyl]-3-azabicyclo[3.2.1]octan-8-amine

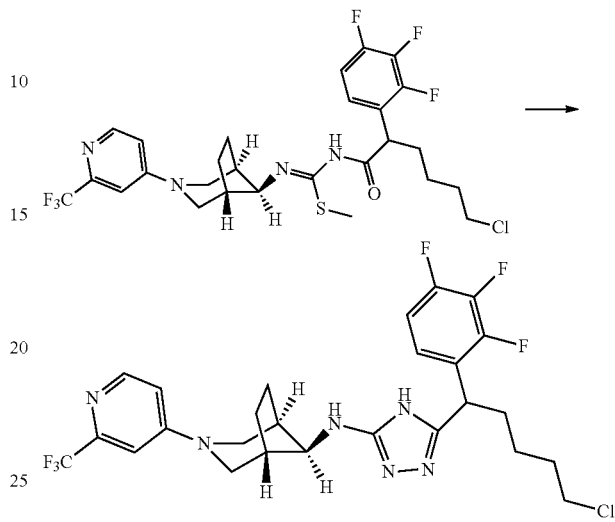

To a solution of 6-chloro-N—[(Z)—C-methylsulfanyl-N-[(1R,5S,8S)-3-[2-(trifluoromethyl)-4-pyridyl]-3-azabicyclo[3.2.1]octan-8-yl]carbonimidoyl]-2-(2,3,4-trifluorophenyl)hexanamide (95 mg, 0.15 mmol) in DMF (1 mL) was added hydrazine 1M in THF (2 mL, 2 mmol). The reaction mixture was stirred at RT for six hours and concentrated under vacuo. A column chromatography (SiO$_2$, CH$_2$Cl$_2$/MeOH) gave 10 mg (11%) of (1S,5R,8S)—N-[5-[5-chloro-1-(2,3,4-trifluorophenyl)pentyl]-4H-1,2,4-triazol-3-yl]-3-[2-(trifluoromethyl)-4-pyridyl]-3-azabicyclo[3.2.1]octan-8-amine as a white solid. MS (ES+) m/z: 573.3 [(M+H)$^+$].

Step 6: N-[(1R,5S,8S)-3-[2-(trifluoromethyl)-4-pyridyl]-3-azabicyclo[3.2.1]octan-8-yl]-9-(2,3,4-trifluorophenyl)-6,7,8,9-tetrahydro-5H-[1,2,4]triazolo[1,5-a]azepin-2-amine

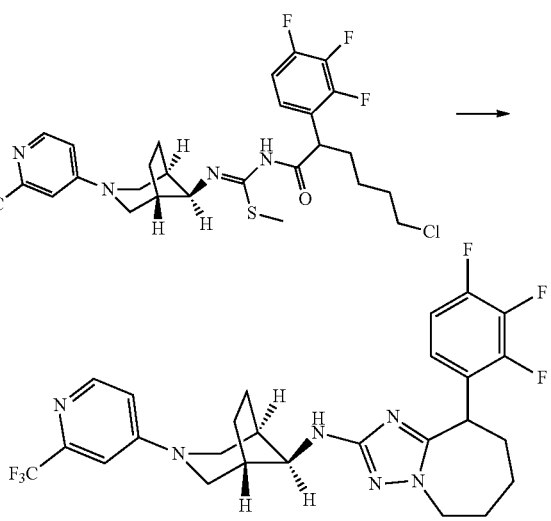

To a solution of (1S,5R,8S)—N-[5-[5-chloro-1-(2,3,4-trifluorophenyl)pentyl]-4H-1,2,4-triazol-3-yl]-3-[2-(trifluoromethyl)-4-pyridyl]-3-azabicyclo[3.2.1]octan-8-amine (26 mg, 0.045 mmol) in DMF (2 mL) was added $K_2CO_3$ (25 mg, 0.18 mmol) and KI (15 mg, 0.090 mmol). The reaction mixture was heated at 70° C. for 2 hours and concentrated under vacuo. A column chromatography ($SiO_2$, $CH_2Cl_2$/MeOH) gave 9 mg (37%) of N-[(1R,5S,8S)-3-[2-(trifluoromethyl)-4-pyridyl]-3-azabicyclo[3.2.1]octan-8-yl]-9-(2,3,4-trifluorophenyl)-6,7,8,9-tetrahydro-5H-[1,2,4]triazolo[1,5-a]azepin-2-amine as a white solid. MS (ES+) m/z: 536.2 [(M+H)$^+$].

Example 2

9-[4-(trifluoromethyl)phenyl]-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine

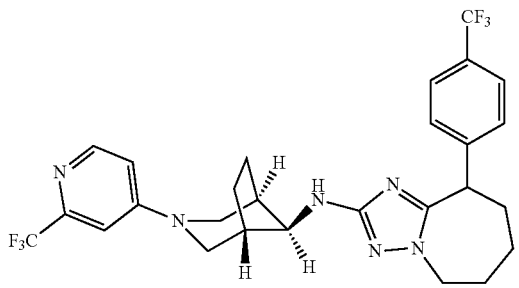 [SMILES: FC(F)(F)c1ccc(C2CCCCn3nc(N[C@@H]4[C@@H]5CC[C@H]4CN(c4ccnc(C(F)(F)F)c4)C5)nc32)cc1]

In analogy to example 1 preparation, using the intermediates 8-5 and 12-2 was prepared 3 mg of the title compound as a white solid. MS (ES+) m/z: 551.3 [(M+H)$^+$].

Example 3

N-[(1R,5S,8S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine

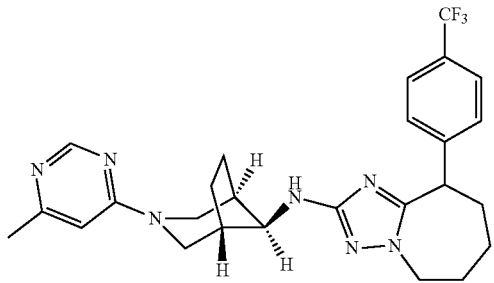

In analogy to example 1 preparation, using the intermediates 8-1 and 12-2 was prepared 20 mg of the title compound as a white solid. MS (ES+) m/z: 498.3 [(M+H)$^+$].

Examples 4 and 5

(9S)—N-[(1R,5S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine and (9R)—N-[(1R,5S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine

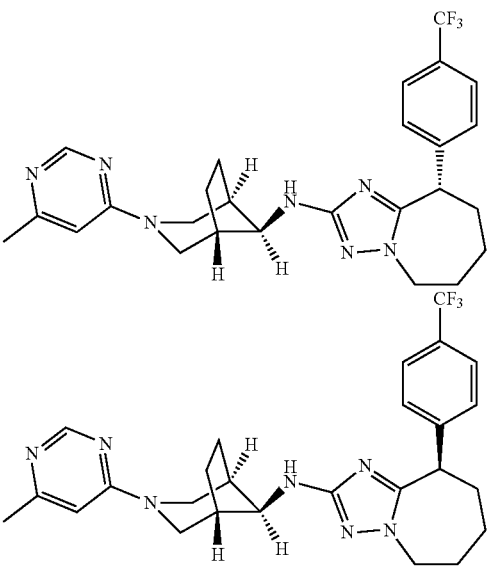

A chiral HPLC separation of the racemic N-[(1R,5S,8S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine (example 3) on Reprosil Chiral NR yielded the titles compounds as white solids 40 mg, MS (ES+) m/z: 498.1 [(M+H)$^+$] and 43 mg, MS (ES+) m/z: 498.1 [(M+H)$^+$].

Example 6

9-(4-chlorophenyl)-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine

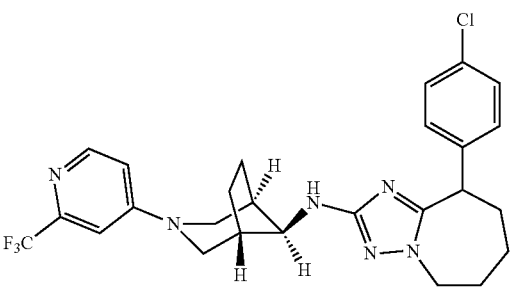 [SMILES: FC(F)(F)c1cc(N2C[C@H]3CC[C@@H](C2)[C@@H]3Nc2nc3n(n2)CCCCC3c2ccc(Cl)cc2)ccn1]

In analogy to example 1 preparation, using the intermediates 8-5 and 12-3 was prepared 35 mg of the title compound as a white solid. MS (ES+) m/z: 517.3 [(M+H)$^+$].

Example 7

9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine

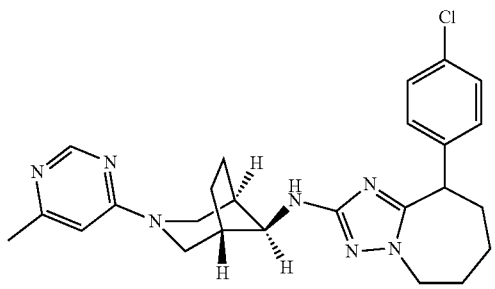 [SMILES: Cc1cc(N2C[C@H]3CC[C@@H](C2)[C@@H]3Nc2nc3n(n2)CCCCC3c2ccc(Cl)cc2)ncn1]

In analogy to example 1 preparation, using the intermediates 8-1 and 12-3 was prepared 19 mg of the title compound as a white solid. MS (ES+) m/z: 464.2 [(M+H)⁺].

Examples 8 and 9

(9S)-9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine and (9R)-9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine

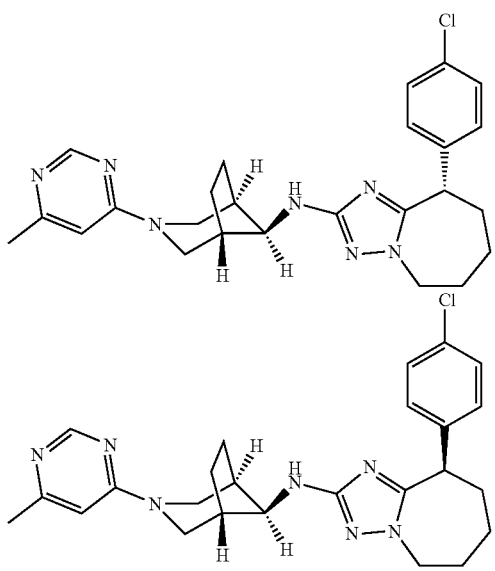

A chiral HPLC separation of the racemic 9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine (example 7) on Reprosil Chiral NR yielded the titles compounds as white solids 8 mg, MS (ES+) m/z: 464.2 [(M+H)⁺] and 8 mg, MS (ES+) m/z: 464.2 [(M+H)⁺].

Example 10

9-[3-(trifluoromethyl)phenyl]-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine

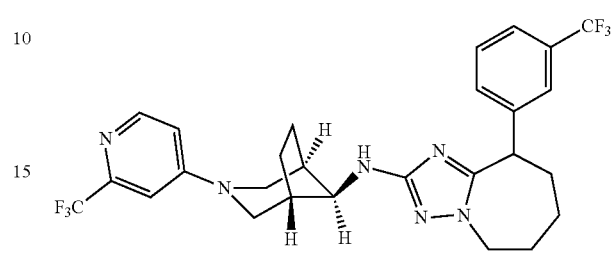

In analogy to example 1 preparation, using the intermediates 8-5 and 12-4 was prepared 19 mg of the title compound as a colorless oil. MS (ES+) m/z: 551.3 [(M+H)⁺].

Example 11

N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine

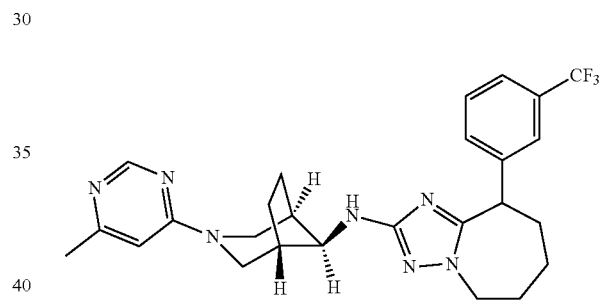

In analogy to example 1 preparation, using the intermediates 8-1 and 12-4 was prepared 55 mg of the title compound as a white solid. MS (ES+) m/z: 498.3 [(M+H)⁺].

Examples 12 and 13

(9S)—N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine and (9R)—N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine

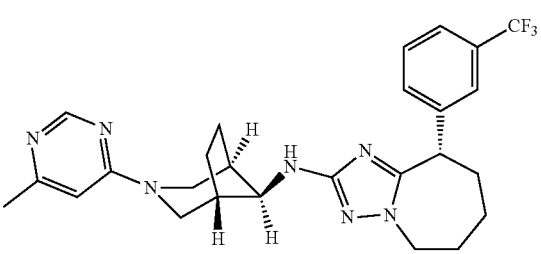 [SMILES: Cc1cc(N2C[C@H]3CC[C@@H](C2)[C@@H]3Nc2nc3n(n2)CCCCC3c2cccc(C(F)(F)F)c2)ncn1]

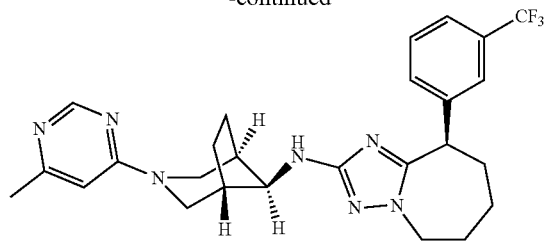

A chiral HPLC separation of the racemic N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (example 11) on Reprosil Chiral NR yielded the titles compounds as white solids 24 mg, MS (ES+) m/z: 498.3 [(M+H)+] and 25 mg, MS (ES+) m/z: 498.3 [(M+H)+].

Example 14

N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

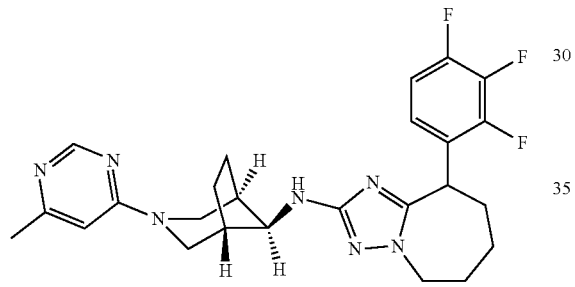

In analogy to example 1 preparation, using the intermediates 8-1 and 12-1 was prepared 34 mg of the title compound as a white solid. MS (ES+) m/z: 484.2 [(M+H)+].

Examples 15 and 16

(9S)—N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and (9R)—N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

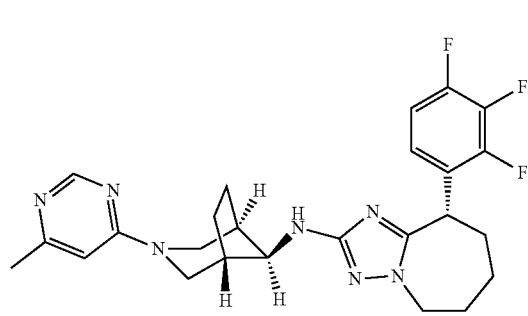 [SMILES: Cc1cc(N2C[C@H]3CC[C@@H](C2)[C@@H]3Nc2nc3n(n2)CCCCC3c2ccc(F)c(F)c2F)ncn1]

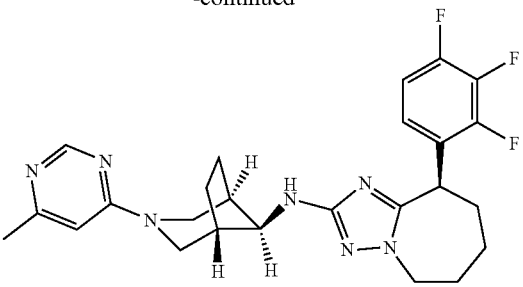

A chiral HPLC separation of the racemic N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (example 14) on Reprosil Chiral NR yielded the titles compounds as white solids 20 mg, MS (ES+) m/z: 484.2 [(M+H)+] and 25 mg, MS (ES+) m/z: 484.2 [(M+H)+].

Example 17

N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

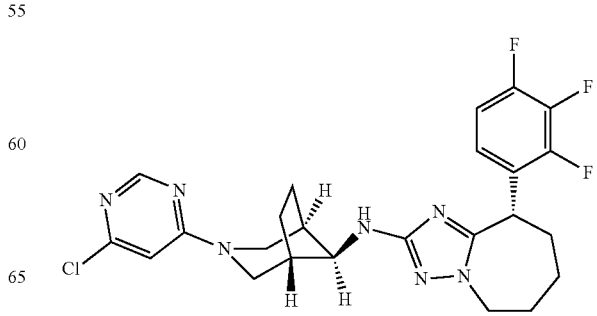

In analogy to example 1 preparation, using the intermediates 8-3 and 12-1 was prepared 37 mg of the title compound as a white solid. MS (ES+) m/z: 504.2 [(M+H)+].

Examples 18 and 19

(9S)—N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and (9R)—N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine -continued

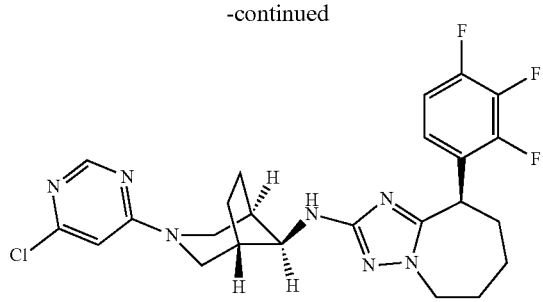

A chiral HPLC separation of the racemic N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (example 17) on Reprosil Chiral NR yielded the titles compounds as white solids 30 mg, MS (ES+) m/z: 504.2 [(M+H)+] and 32 mg, MS (ES+) m/z: 504.2 [(M+H)+].

Example 20

N-[(1R,5S,8S)-3-(2-methoxy-4-pyridyl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

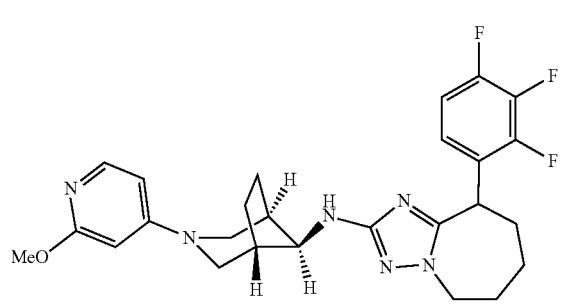 [SMILES: COc1cc(N2C[C@H]3CC[C@@H](C2)[C@@H]3Nc2nc3n(n2)CCCCC3c2ccc(F)c(F)c2F)ccn1]

In analogy to example 1 preparation, using the intermediates 8-6 and 12-1 was prepared 25 mg of the title compound as a white solid. MS (ES+) m/z: 499.3 [(M+H)+].

Example 21

N-[(1R,5S,8S)-3-(6-methoxypyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

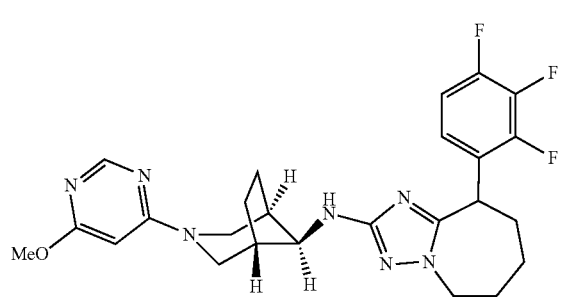 [SMILES: COc1cc(N2C[C@H]3CC[C@@H](C2)[C@@H]3Nc2nc3n(n2)CCCCC3c2ccc(F)c(F)c2F)ncn1]

Step 1: Tert-butyl (1R,5S,8S)-8-[[9-(2,3,4-trifluorophenyl)-6,7,8,9-tetrahydro-5H-[1,2,4]triazolo[1,5-a]azepin-2-yl]amino]-3-azabicyclo[3.2.1]octane-3-carboxylate

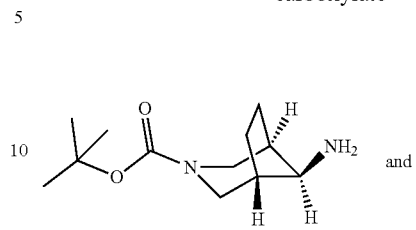
and

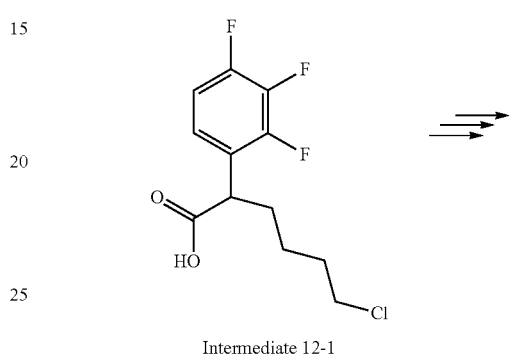

Intermediate 12-1

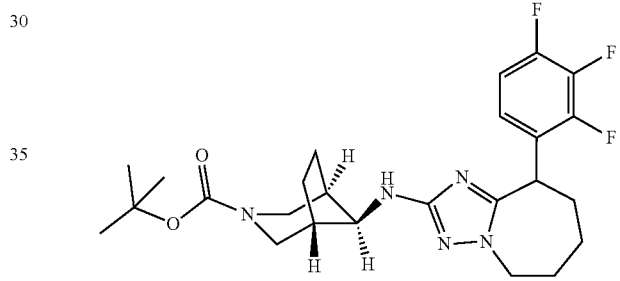

In analogy to example 1 preparation, using the commercially available tert-butyl (1R,5S,8S)-8-amino-3-azabicyclo[3.2.1]octane-3-carboxylate and the intermediate 12-1 was prepared 404 mg of tert-butyl (1R,5S,8S)-8-[[9-(2,3,4-trifluorophenyl)-6,7,8,9-tetrahydro-5H-[1,2,4]triazolo[1,5-a]azepin-2-yl]amino]-3-azabicyclo[3.2.1]octane-3-carboxylate as a white solid. MS (ES+) m/z: 492.3 [(M+H)+].

Step 2: N-[(1R,5S,8S)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

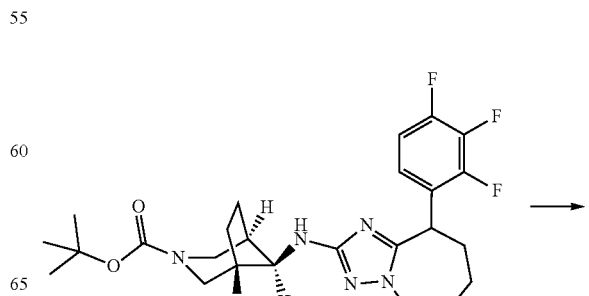

-continued

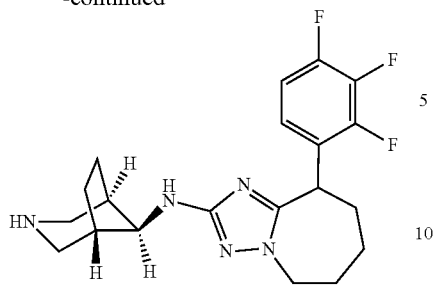

To a stirred solution of tert-butyl (1R,5S,8S)-8-[[9-(2,3,4-trifluorophenyl)-6,7,8,9-tetrahydro-5H-[1,2,4]triazolo[1,5-a]azepin-2-yl]amino]-3-azabicyclo[3.2.1]octane-3-carboxylate (400 mg, 0.81 mmol) in CH$_2$Cl$_2$ (4 mL) was added TFA (0.50 mL, 6.5 mmol). The reaction mixture was stirred at RT for 6 hours and then evaporated to dryness under vacuo. The residue was dissolved in CH$_2$Cl$_2$ and then washed with an aqueous NaHCO$_3$ solution. The organic phase was dried over Na$_2$SO$_4$ and concentrated under vacuo to give 320 mg (89%) of N-[(1R,5S,8S)-3-azabicyclo[3.2.1]octan-8-yl]-9-(2,3,4-trifluorophenyl)-6,7,8,9-tetra hydro-5H-[1,2,4]triazolo[1,5-a]azepin-2-amine as a light yellow solid. MS (ES+) m/z: 392.3 [(M+H)$^+$].

Step 3: N-[(1R,5S,8S)-3-(6-methoxypyrimidin-4-yl)-3-azabicyclo[3.2.]octan-8-yl]-9-(2,3,4-trifluorophenyl)-6,7,8,9-tetrahydro-5H-[1,2,4]triazolo[1,5-a]azepin-2-amine

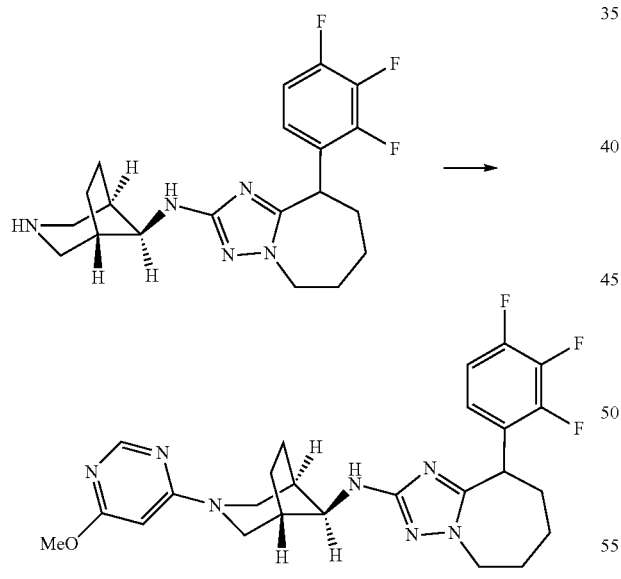

To a stirred solution of N-[(1R,5S,8S)-3-azabicyclo[3.2.1]octan-8-yl]-9-(2,3,4-trifluorophenyl)-6,7,8,9-tetra hydro-5H-[1,2,4]triazolo[1,5-a]azepin-2-amine (35 mg, 0.089 mmol) in NMP (2 mL) was added 4-chloro-6-methoxy-pyrimidine (12.5 mg, 0.089 mmol) and NEt(iPr)$_2$ (0.047 mL, 0.268 mmol). The reaction mixture was heated at 100° C. for one hour and then evaporated under vacuo. Purification by preparative HPLC gave 16 mg (36%) of N-[(1R,5S,8S)-3-(6-methoxypyrimidin-4-yl)-3-azabicyclo[3.2.1]octan-8-yl]-9-(2,3,4-trifluorophenyl)-6,7,8,9-tetra hydro-5H-[1,2,4]triazolo[1,5-a]azepin-2-amine as a white solid. MS (ES+) m/z: 500.4 [(M+H)$^+$].

Example 22

N-[(1R,5S,8S)-3-(5-fluoro-6-methyl-pyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

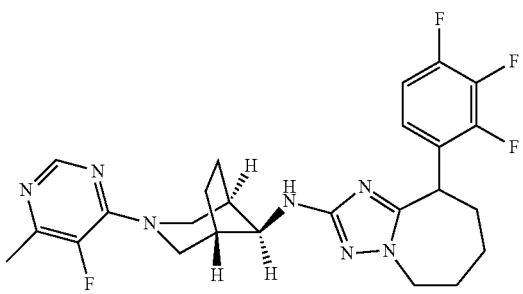 [SMILES: Cc1ncnc(N2C[C@H]3CC[C@@H](C2)[C@@H]3Nc2nc3n(n2)CCCCC3c2ccc(F)c(F)c2F)c1F]

In an analogy from example 21, step 3, from N-[(1R,5S,8S)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and 4-chloro-5-fluoro-6-methyl-pyrimidine was prepared 20 mg of the title product as a white solid. MS (ES+) m/z: 502.4 [(M+H)$^+$].

Example 23

N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

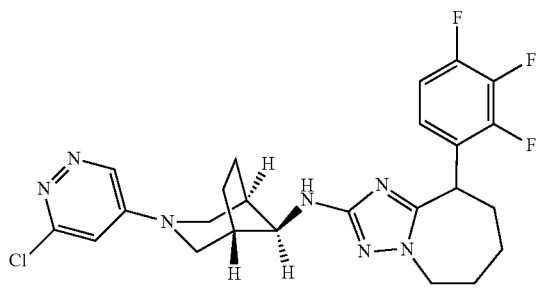 [SMILES: Fc1ccc(C2CCCCn3nc(N[C@@H]4[C@@H]5CC[C@H]4CN(c4cnnc(Cl)c4)C5)nc32)c(F)c1F]

In an analogy from example 21, step 3, from N-[(1R,5S,8S)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and 3,5-dichloropyridazine was prepared 12 mg of the title product as a white solid. MS (ES+) m/z: 504.2 [(M+H)$^+$].

Examples 24 and 25

(9S)—N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and (9R)—N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

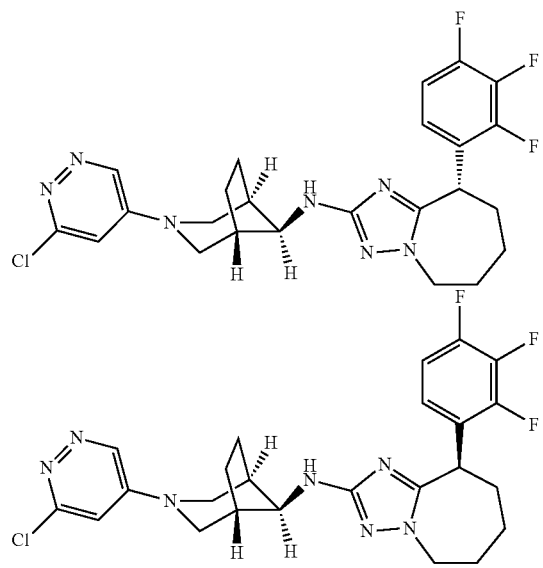

A chiral HPLC separation of the racemic N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (example 23) on Reprosil Chiral NR yielded the titles compounds as white solids 5 mg, MS (ES+) m/z: 504.2 [(M+H)$^+$] and 6 mg, MS (ES+) m/z: 504.2 [(M+H)$^+$].

Example 26

N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

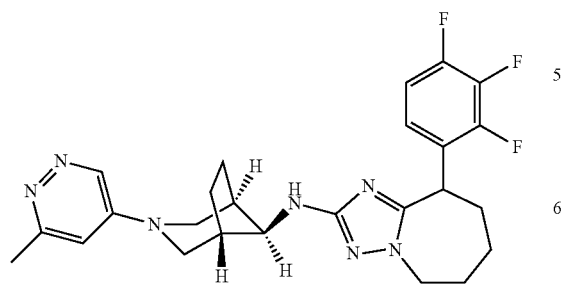

In an analogy from example 21, step 3, from N-[(1R,5S,8S)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and 5-chloro-3-methyl-pyridazine was prepared 10 mg of the title product as a white solid. MS (ES+) m/z: 484.2 [(M+H)$^+$].

Examples 27 and 28

(9S)—N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and (9R)—N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

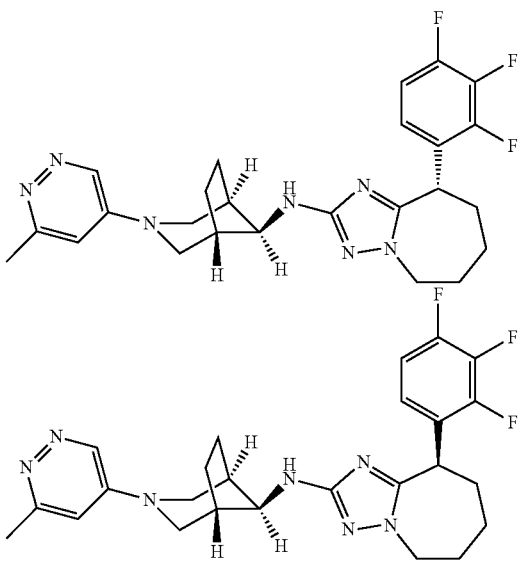

A chiral HPLC separation of the racemic N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (example 26) on Reprosil Chiral NR yielded the titles compounds as white solids 4 mg, MS (ES+) m/z: 484.2 [(M+H)$^+$] and 4 mg, MS (ES+) m/z: 484.2 [(M+H)$^+$].

Example 29

N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

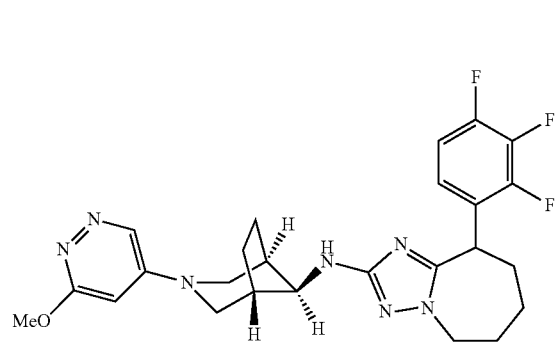 [SMILES: COc1cc(N2C[C@H]3CC[C@@H](C2)[C@@H]3Nc2nc3n(n2)CCCCC3c2ccc(F)c(F)c2F)cnn1]

To a stirred solution of N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (example 23) (10 mg, 0.019 mmol) in MeOH (1 mL) was added NaOMe (25% sol. in MeOH; 23 µL, 0.10 mmol). The reaction was stirred at 120° C. for 5 hours, concentrated under vauco and a purification by preparative HPLC afforded the title product (7 mg, 66%) as a white solid. MS (ES+) m/z: 500.2 [(M+H)⁺].

Examples 30 and 31

(9S)—N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine and (9R)—N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine

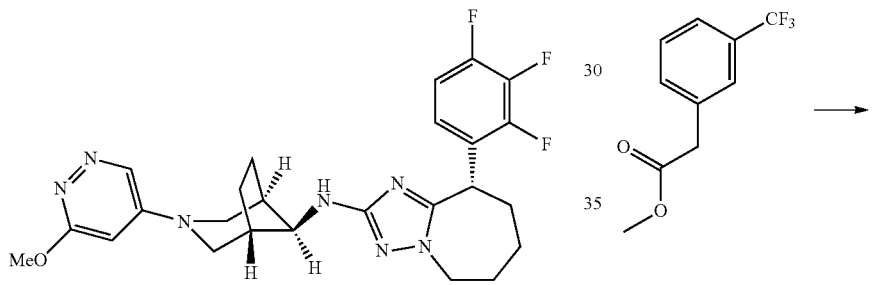

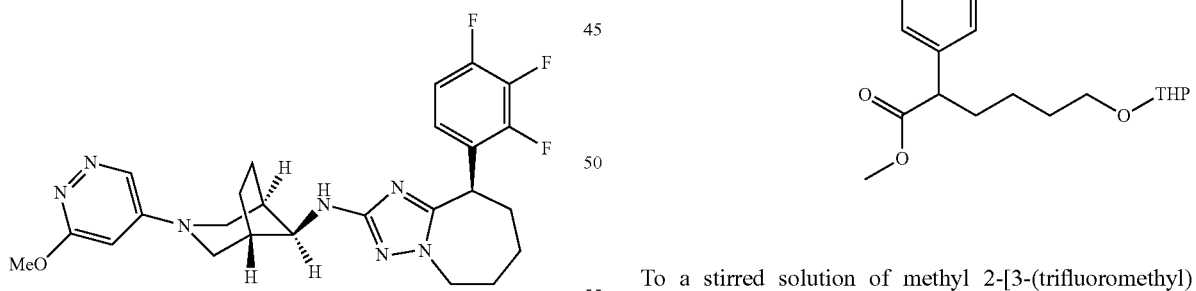

A chiral HPLC separation of the racemic N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine (example 29) on Reprosil Chiral NR yielded the titles compounds as white solids 5 mg, MS (ES+) m/z: 500.2 [(M+H)⁺] and 6 mg, MS (ES+) m/z: 500.2 [(M+H)⁺].

Example 32

N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine

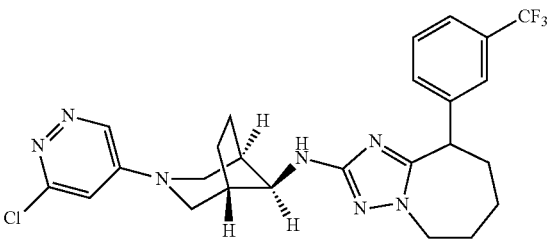 [SMILES: FC(F)(F)c1cccc(C2CCCCn3nc(N[C@@H]4[C@@H]5CC[C@H]4CN(c4cnnc(Cl)c4)C5)nc32)c1]

Step 1: Methyl 6-tetrahydropyran-2-yloxy-2-[3-(trifluoromethyl)phenyl]hexanoate

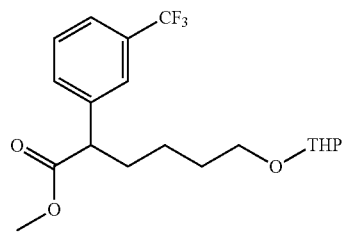

To a stirred solution of methyl 2-[3-(trifluoromethyl)phenyl]acetate (6.33 g, 29 mmol) in DMF (45 mL) at 0° C. was added NaH (60%, 1.28 g, 31.9 mmol). The reaction mixture was stirred for 1 hour and then cannulated dropwise into a solution of 2-(4-bromobutoxy)tetrahydropyran (6.88 g, 29 mmol) in DMF (45 mL) also at 0° C. The reaction was further stirred at RT for one hour and poured onto an aqueous saturated solution of NH₄Cl. The product was extracted with EtOAc, and the combined organic phase was dried over Na₂SO₄ and concentrated under vacuo. A column chromatography (SiO₂, Heptane/EtOAc) gave 7.82 g (72%) of methyl 6-tetrahydropyran-2-yloxy-2-[3-(trifluoromethyl)phenyl]hexanoate as a light yellow oil.

Step 2: 6-Tetrahydropyran-2-yloxy-2-[3-(trifluoromethyl)phenyl]hexanehydrazide

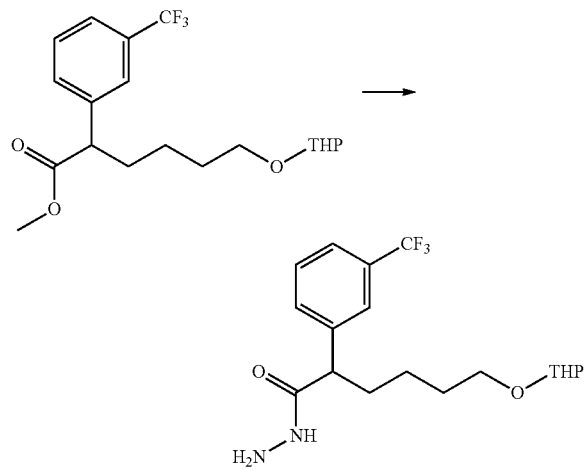

To a stirred solution of methyl 6-tetrahydropyran-2-yloxy-2-[3-(trifluoromethyl)phenyl]hexanoate (7.82 g, 20.9 mmol) in MeOH (70 mL) was added hydrazine hydrate (16.9 mL, 272 mmol). The reaction mixture was stirred at 80° C. for 17 hours and concentrated under vacuo. The residue was diluted with water and the product extracted with EtOAc. The combined organic phase was dried over $Na_2SO_4$ and concentrated under vacuo to give 7.81 g (99%) of 6-tetrahydropyran-2-yloxy-2-[3-(trifluoromethyl)phenyl]hexanehydrazide as a colorless oil. MS (ES+) m/z: 375.2 $[(M+H)^+]$.

Step 3: 5-[5-Tetrahydropyran-2-yloxy-1-[3-(trifluoromethyl)phenyl]pentyl]-4H-1,2,4-triazol-3-amine

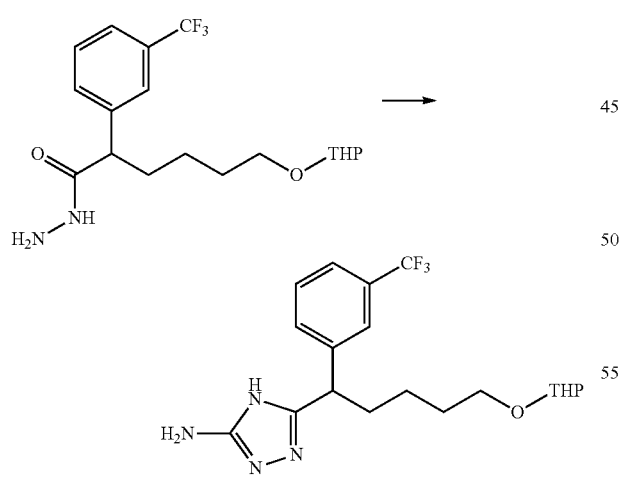

In a sealed reactor, 6-tetrahydropyran-2-yloxy-2-[3-(trifluoromethyl)phenyl]hexanehydrazide (7.82 g, 20.9 mmol) was dissolved in 2-propanol (55 mL). $Et_3N$ (8.7 mL, 62.7 mmol) and 2-methyl-2-thiopseudourea sulfate (2.91 g, 10.4 mmol) were added and the reaction mixture was heated at 130° C. over night. The reaction mixture was then cooled to RT, concentrated under vacuo and the residue diluted with $CH_2Cl_2$ and then washed with brine. The organic phase was dried over $Na_2SO_4$, concentrated under vacuo. A column chromatography ($SiO_2$, $CH_2Cl_2$/MeOH) gave (4.89 g, 59%) of 5-[5-Tetrahydropyran-2-yloxy-1-[3-(trifluoromethyl)phenyl]pentyl]-4H-1,2,4-triazol-3-amine as a white foam. MS (ES+) m/z: 399.3 $[(M+H)^+]$.

Step 4: 5-(5-bromo-4H-1,2,4-triazol-3-yl)-5-[3-(trifluoromethyl)phenyl]pentan-1-ol

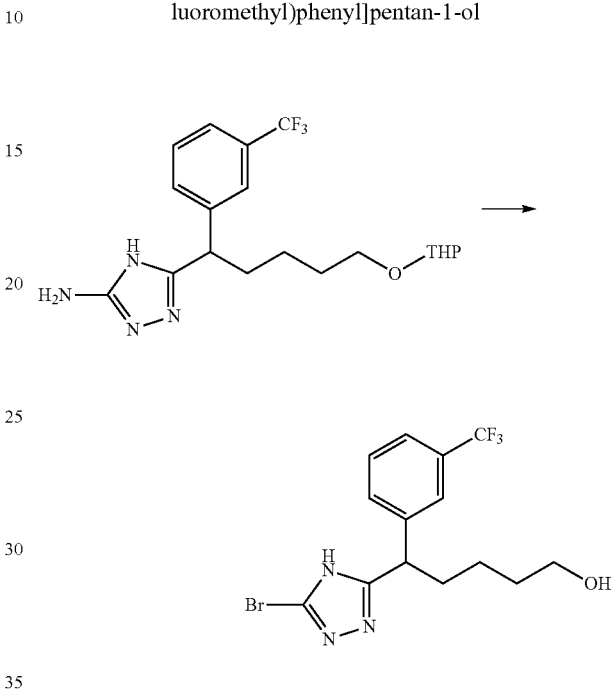

To a black solution of tert-butyl nitrite (2.11 g, 2.43 mL, 18.4 mmol) and cupric bromide (4.11 g, 18.4 mmol) in $CH_3CN$ (40 mL) at 60° C. was added portion wise 5-[5-tetrahydropyran-2-yloxy-1-[3-(trifluoromethyl)phenyl]pentyl]-4H-1,2,4-triazol-3-amine (4.89 g, 12.3 mmol). The reaction mixture was then heated at 75° C. for one hour and cooled down to RT. HCl 2N (3 mL) was added and stirring was continued 30 minutes. The reaction mixture was concentrated under vacuo, and the residue diluted with EtOAc and washed with water. The organic phase was dried over $Na_2SO_4$, concentrated under vacuo. A column chromatography ($SiO_2$, Heptane/EtOAc) gave 2.7 g (38%) of 5-(5-bromo-4H-1,2,4-triazol-3-yl)-5-[3-(trifluoromethyl)phenyl]pentan-1-ol as a yellow foam. MS (ES+) m/z: 378.1 $[(M+H)^+]$.

Step 5: 2-bromo-9-[3-(trifluoromethyl)phenyl-]6,7,8,9-tetrahydro-5H-[1,2,4]triazolo[1,5-a]azepine

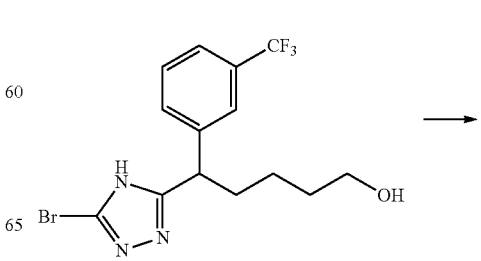

-continued

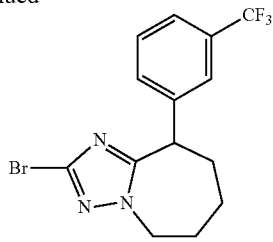

To a solution of 5-(5-bromo-4H-1,2,4-triazol-3-yl)-5-[3-(trifluoromethyl)phenyl]pentan-1-ol (1.31 g, 2.25 mmol) and triphenylphosphine (0.866 g, 3.38 mmol) in THF (25 mL) at −10° C. was added DEAD (0.53 mL, 3.38 mmol). The reaction mixture was further stirred for 30 minutes at this temperature and then poured into water. The product was extracted with EtOAc and the combined organic phase was dried over $Na_2SO_4$ and concentrated under vacuo. A column chromatography ($SiO_2$, Heptane/EtOAc) gave 0.51 g (63%) of 2-bromo-9-[3-(trifluoromethyl)phenyl]-6,7,8,9-tetrahydro-5H-[1,2,4]triazolo[1,5-a]azepine as white solid. MS (ES+) m/z: 360.0 [(M+H)$^+$].

Step 6: N-[(1R,5S,8S)-3-(6-chloropyridazin-4-yl)-3-azabicyclo[3.2.1]octan-8-yl]-9-[3-(trifluoro methyl)phenyl]-6,7,8,9-tetrahydro-5H-[1,2,4]triazolo[1,5-a]azepin-2-amine

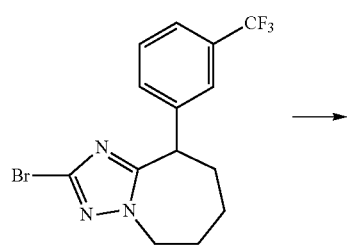

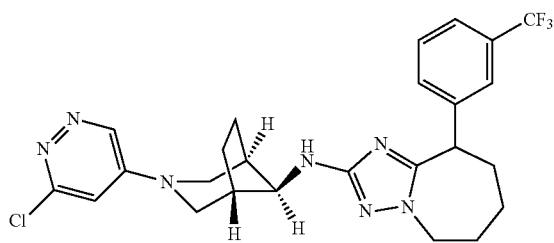

Using the general Buchwald procedure 1, from 2-bromo-9-[3-(trifluoromethyl)phenyl]-6,7,8,9-tetrahydro-5H-[1,2,4]triazolo[1,5-a]azepine (99 mg, 0.41 mmol) and (1R,5S,8S)-3-(6-chloropyridazin-4-yl)-3-azabicyclo[3.2.1]octan-8-amine (intermediate 8-7) was prepared 53 mg (37%) of the title product as a light yellow solid. MS (ES+) m/z: 518.2 [(M+H)$^+$].

Examples 33 and 34

(9S)—N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine and (9R)—N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine

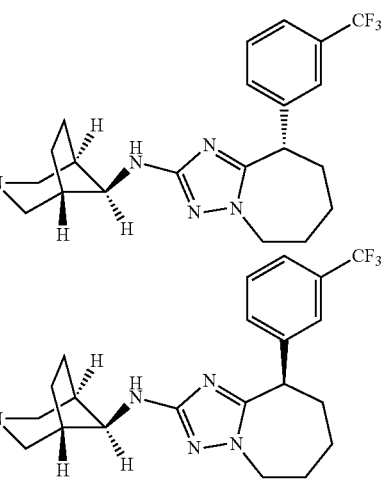

A chiral HPLC separation of the racemic N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (example 32) on Reprosil Chiral NR yielded the titles compounds as white solids 15 mg, MS (ES+) m/z: 518.2 [(M+H)$^+$] and 15 mg, MS (ES+) m/z: 518.2 [(M+H)$^+$].

Example 35

N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine

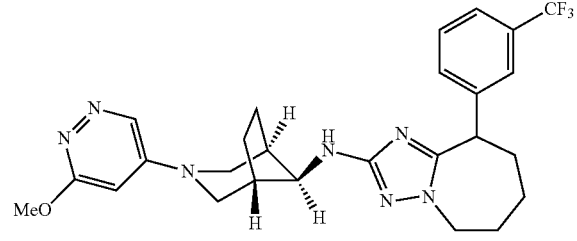 [SMILES: COc1cc(N2C[C@H]3CC[C@@H](C2)[C@@H]3Nc2nc3n(n2)CCCCC3c2cccc(C(F)(F)F)c2)cnn1]

Using the general Buchwald procedure 1, from 2-bromo-9-[3-(trifluoromethyl)phenyl]-6,7,8,9-tetrahydro-5H-[1,2,4]triazolo[1,5-a]azepine (described in example 32, step 5) and (1R,5S,8S)-3-(6-methoxypyridazin-4-yl)-3-azabicyclo[3.2.1]octan-8-amine (intermediate 8-8) was prepared 87 mg of the title product as a white solid. MS (ES+) m/z: 514.3 [(M+H)$^+$].

Examples 36 and 37

(9S)—N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine and (9R)—N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine

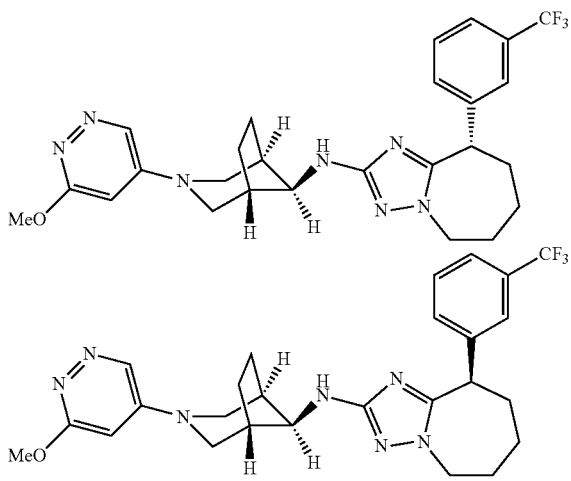

A chiral HPLC separation of the racemic N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (example 35) on Reprosil Chiral NR yielded the titles compounds as white solids 20 mg, MS (ES+) m/z: 514.3 [(M+H)$^+$] and 21 mg, MS (ES+) m/z: 514.3 [(M+H)$^+$].

Example 38

N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine

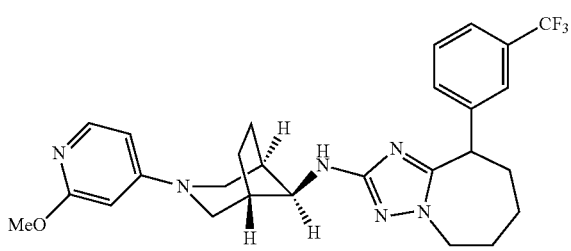 [SMILES: COc1cc(N2C[C@H]3CC[C@@H](C2)[C@@H]3Nc2nc3n(n2)CCCCC3c2cccc(C(F)(F)F)c2)ccn1]

Using the general Buchwald procedure 1, from 2-bromo-9-[3-(trifluoromethyl)phenyl]-6,7,8,9-tetrahydro-5H-[1,2,4]triazolo[1,5-a]azepine (described in example 32, step 5) and (1R,5S,8S)-3-(2-methoxy-4-pyridyl)-3-azabicyclo[3.2.1]octan-8-amine (intermediate 8-6) was prepared 50 mg of the title product as a white solid. MS (ES+) m/z: 513.2 [(M+H)$^+$].

Examples 39 and 40

(9S)—N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine and (9R)—N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine

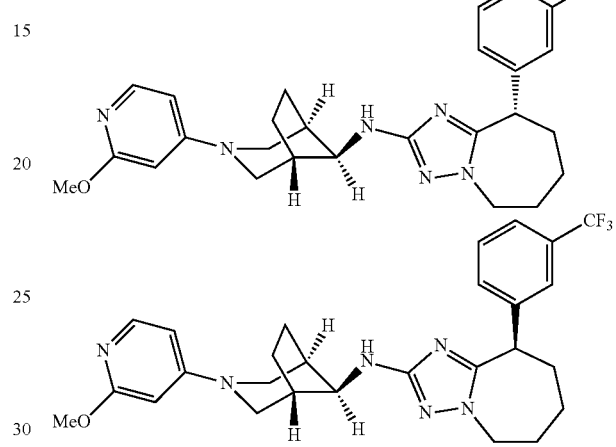

A chiral HPLC separation of the racemic N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine (example 38) on Reprosil Chiral NR yielded the titles compounds as white solids 14 mg, MS (ES+) m/z: 513.2 [(M+H)$^+$] and 14 mg, MS (ES+) m/z: 513.2 [(M+H)$^+$].

Example 41

9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine

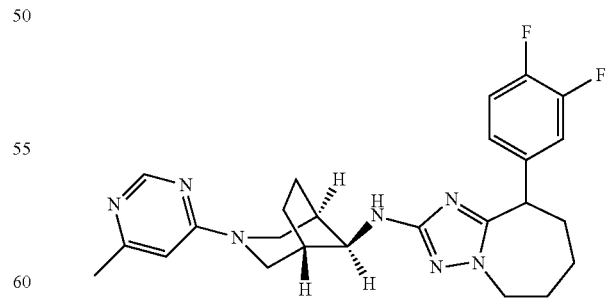

In analogy to example 32, from methyl 2-(3,4-difluorophenyl)acetate and (1R,5S,8S)-3-(6-methylpyrimidin-4-yl)-3-azabicyclo[3.2.1]octan-8-amine (intermediate 8-1) was prepared 26 mg of the title product as a white solid. MS (ES+) m/z: 466.3 [(M+H)$^+$].

Examples 42 and 43

(9S)-9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine and (9R)-9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine

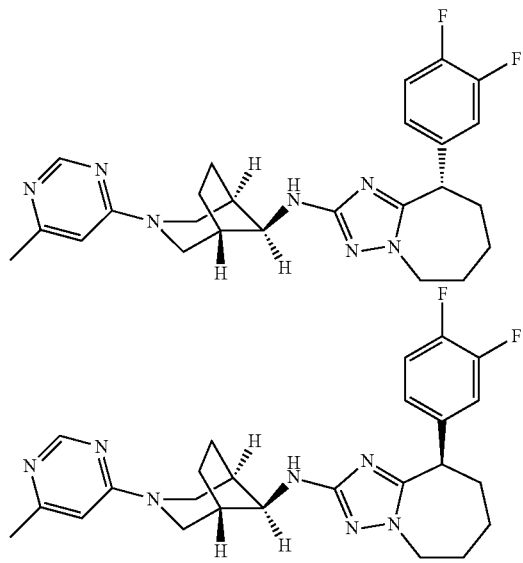

A chiral HPLC separation of the racemic 9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine (example 41) on Reprosil Chiral NR yielded the titles compounds as white solids 8 mg, MS (ES+) m/z: 466.3 [(M+H)$^+$] and 7 mg, MS (ES+) m/z: 466.3 [(M+H)$^+$].

The invention claimed is:

1. A compound of formula I, I-1 or I-2,

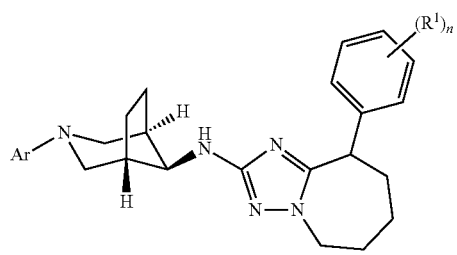

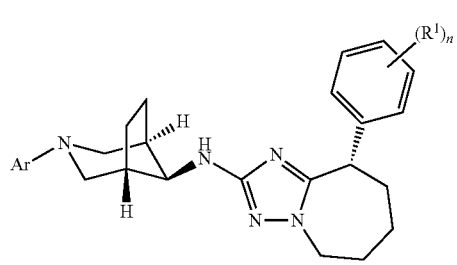

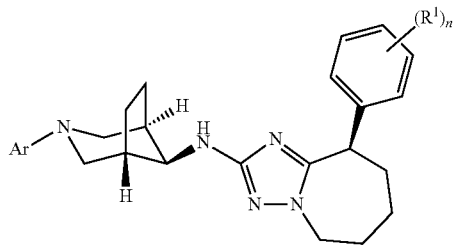

wherein:

n is 1, 2 or 3;

R$^1$ is hydrogen, lower alkyl, lower alkyl substituted by halogen, halogen, lower alkoxy, or lower alkoxy substituted by halogen;

R$^1$ may be different if n=2 or 3;

Ar is a six membered heteroaryl group, selected from:

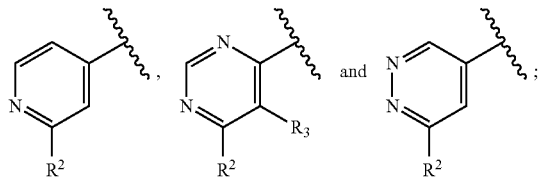

wherein:

R$^2$ is hydrogen, lower alkyl, lower alkyl substituted by halogen, halogen or lower alkoxy; and R$^3$ is hydrogen or halogen;

or a pharmaceutically active acid addition salt thereof.

2. A compound of formula IA, IA-1 or IA-2,

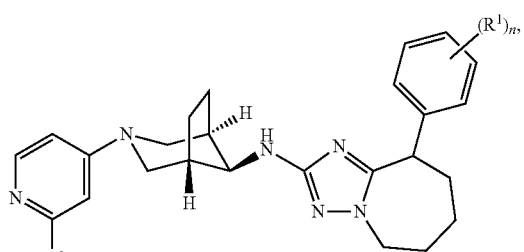

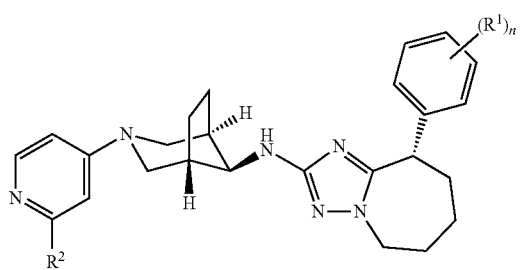

IA-2

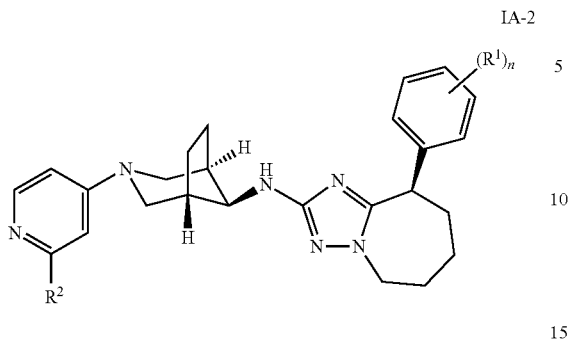

wherein:

n is 1, 2 or 3;

R¹ is hydrogen, lower alkyl, lower alkyl substituted by halogen, halogen, lower alkoxy, or lower alkoxy substituted by halogen;

R¹ may be different if n=2 or 3;

and

R² is hydrogen, lower alkyl, lower alkyl substituted by halogen, halogen or lower alkoxy;

or a pharmaceutically active acid addition salt thereof.

3. A compound selected from:

N-[(1R,5S,8S)-3-[2-(trifluoromethyl)-4-pyridyl]-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

9-[4-(trifluoromethyl)phenyl]-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine;

9-(4-chlorophenyl)-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine;

9-[3-(trifluoromethyl)phenyl]-N-[(1R,5S,8S)-3-[2-(trifluoromethyl)-4-pyridyl]-3-azabicyclo[3.2.1]octan-8-yl]-6,7,8,9-tetrahydro-5H-[1,2,4]triazolo[1,5-a]azepin-2-amine;

N-[(1R,5S,8S)-3-(2-methoxy-4-pyridyl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine;

(9S)—N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine; and (9R)—N-[(1R,5S,8S)-3-(2-methoxy-4-pyridyl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine, or a pharmaceutically active acid addition salt thereof.

4. A compound of formula IB, IB-1 or IB-2,

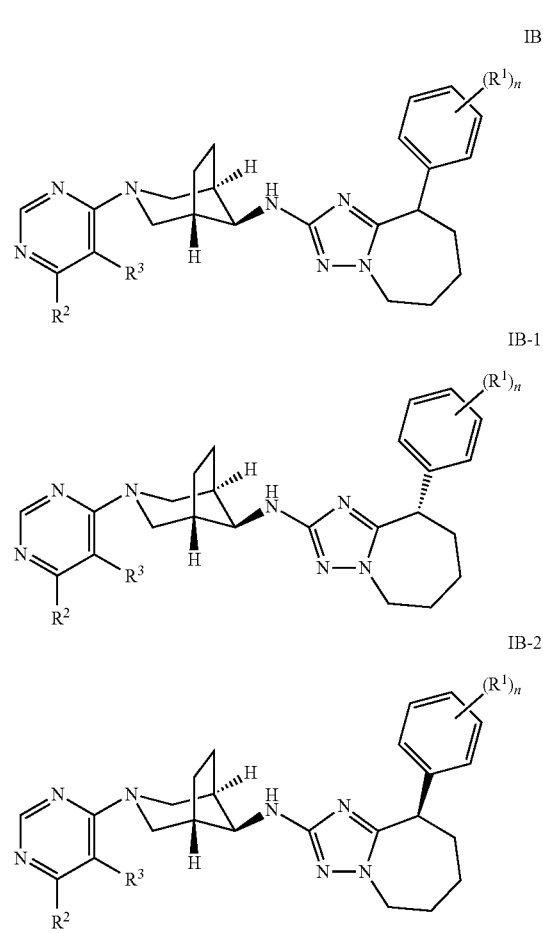

wherein:

n is 1, 2 or 3;

R¹ is hydrogen, lower alkyl, lower alkyl substituted by halogen, halogen, lower alkoxy, or lower alkoxy substituted by halogen;

R¹ may be different if n=2 or 3;

R² is hydrogen, lower alkyl, lower alkyl substituted by halogen, halogen or lower alkoxy; and R³ is hydrogen or halogen;

or a pharmaceutically active acid addition salt thereof.

5. A compound selected from:

N-[(1R,5S,8S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine;

(9S)—N-[(1R,5S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine;

(9R)—N-[(1R,5S)-3-(6-methylpyrimidin-4-yl)-3-azabicyclo[3.2.1]octan-8-yl]-9-[4-(trifluoromethyl)phenyl]-6,7,8,9-tetrahydro-5H-[1,2,4]triazolo[1,5-a]azepin-2-amine;

9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine;

(9S)-9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine;

(9R)-9-(4-chlorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine;

N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine;

(9S)—N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine;

(9R)—N-[(1R,5S,8S)-3-(6-methylpyrimidin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine;

N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9S)—N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9R)—N-[(1R,5S,8S)-3-(6-methylpyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9S)—N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9R)—N-[(1R,5S,8S)-3-(6-chloropyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

N-[(1R,5S,8S)-3-(6-methoxypyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

N-[(1R,5S,8S)-3-(5-fluoro-6-methyl-pyrimidin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine;

(9S)-9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine; and (9R)-9-(3,4-difluorophenyl)-N-[(1R,5S,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine, or a pharmaceutically active acid addition salt thereof.

6. A compound of formula IC, IC-1 or IC-2,

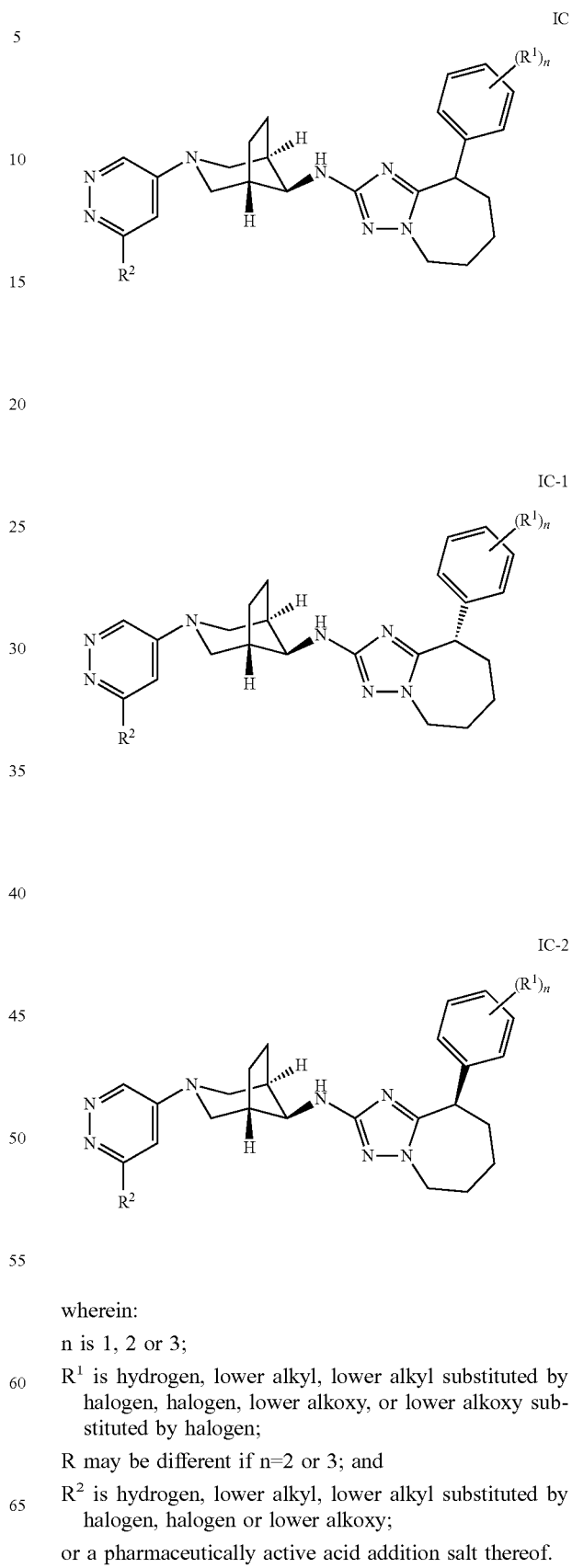

wherein:

n is 1, 2 or 3;

$R^1$ is hydrogen, lower alkyl, lower alkyl substituted by halogen, halogen, lower alkoxy, or lower alkoxy substituted by halogen;

R may be different if n=2 or 3; and $R^2$ is hydrogen, lower alkyl, lower alkyl substituted by halogen, halogen or lower alkoxy;

or a pharmaceutically active acid addition salt thereof.

7. A compound selected from:

N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9S)—N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9R)—N-[(1R,5S,8S)-3-(6-chloropyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9S)—N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9R)—N-[(1R,5S,8S)-3-(6-methylpyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9S)—N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

(9R)—N-[(1R,5S,8S)-3-(6-methoxypyridazin-4-yl)-3-azabicyclo[3.2.1]octan-8-yl]-9-(2,3,4-trifluorophenyl)-6,7,8,9-tetrahydro-5H-[1,2,4]triazolo[1,5-a]azepin-2-amine;

N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine;

(9S)—N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine;

(9R)—N-[(1R,5S,8S)-3-(6-chloropyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine;

N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine;

(9S)—N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine; and (9R)—N-[(1R,5S,8S)-3-(6-methoxypyridazin-4-yl)-3-azabicyclo[3.2.1]octan-8-yl]-9-[3-(trifluoromethyl)phenyl]-6,7,8,9-tetrahydro-5H-[1,2,4]triazolo[1,5-a]azepin-2-amine, or a pharmaceutically active acid addition salt thereof.

8. A process for preparing a compound of formula I as defined in claim 1, which process comprises one of:

a) reacting a compound of formula 7

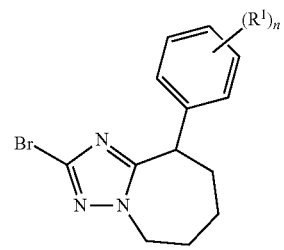

with a compound of formula 8

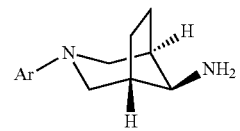

to form a compound of formula I

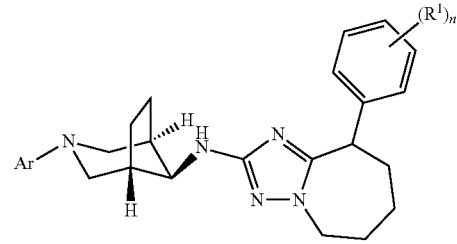

and, optionally, converting the compound obtained into a pharmaceutically acceptable acid addition salt;

b) cyclization of a compound of formula 14

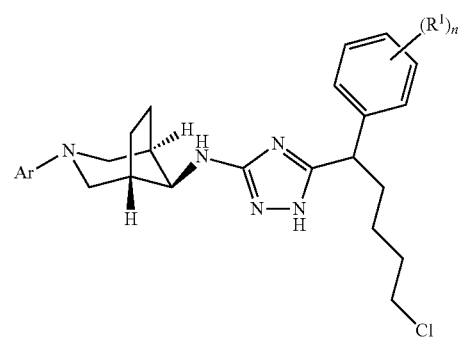

in the presence of KI and K₂CO₃ to a compound of formula I

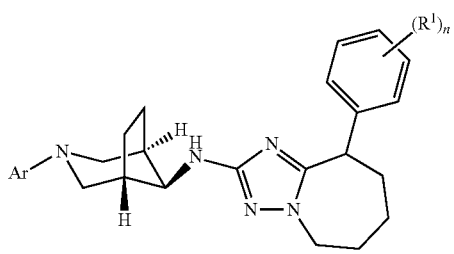

and, optionally, converting the compound obtained into a pharmaceutically acceptable acid addition salt; or c) reacting a compound of formula 16

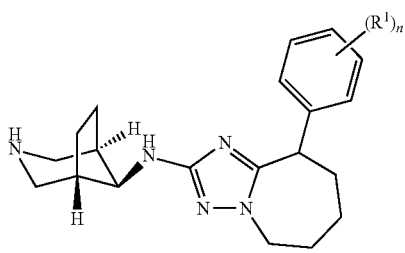

with a compound of formula Ar—X to form a compound of formula I

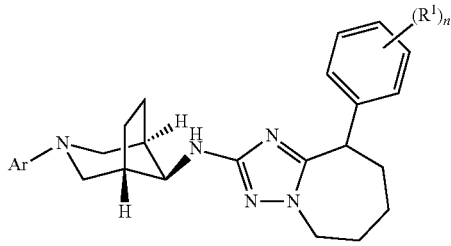

wherein X is halogen, and,
optionally, converting the compound obtained into a pharmaceutically acceptable acid addition salt
d).

9. A compound of formula I prepared by a process according to claim 8.

10. A pharmaceutical preparation containing a compound of formula I of claim 1, or a pharmaceutically acceptable salt thereof, and one or more therapeutically inert carriers.

11. A method for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, which method comprises administering an effective amount of a compound as defined in claim 1 to a person in need thereof.

12. The method of claim 8, further comprising, after any of a), b), or c): separating a racemic compound of formula I by a chiral HPLC separation to produce a compound of formula I-1 or I-2.

* * * * *